US006888017B2

(12) United States Patent
Kuchta et al.

(10) Patent No.: US 6,888,017 B2
(45) Date of Patent: May 3, 2005

(54) METALLOCENE COMPOSITIONS

(75) Inventors: Matthew C. Kuchta, Houston, TX (US); Udo M. Stehling, Vantaa (FI); Robert T. Li, Houston, TX (US); William T. Haygood, Jr., Houston, TX (US); Terry J. Burkhardt, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 330 days.

(21) Appl. No.: 10/066,221

(22) Filed: Jan. 31, 2002

(65) Prior Publication Data

US 2002/0193242 A1 Dec. 19, 2002

Related U.S. Application Data

(62) Division of application No. 09/620,046, filed on Jul. 19, 2000, now Pat. No. 6,380,122.
(60) Provisional application No. 60/215,597, filed on Jun. 30, 2000.

(51) Int. Cl.[7] .............................. C07F 9/00; C07F 11/00; C07F 17/00
(52) U.S. Cl. .............................. 556/11; 556/12; 556/22; 556/23; 556/43; 556/53; 556/58
(58) Field of Search .............................. 556/11, 12, 22, 556/23, 43, 53, 58; 502/103, 117, 152, 155

(56) References Cited

U.S. PATENT DOCUMENTS

| 5,658,997 | A | 8/1997 | Fukuoka et al. ............. 526/127 |
| 5,705,584 | A | 1/1998 | Fukuoka et al. ......... 526/348.2 |
| 5,710,223 | A | 1/1998 | Fukuoka et al. ............. 526/127 |
| 5,723,640 | A | 3/1998 | Fukuoka et al. .............. 556/11 |
| 5,753,769 | A | 5/1998 | Ueda et al. |
| 5,770,753 | A | 6/1998 | Küber et al. |
| 5,786,432 | A | 7/1998 | Küber et al. ................. 526/127 |
| 5,789,634 | A | 8/1998 | Sullivan et al. |
| 5,840,644 | A | 11/1998 | Küber et al. |
| 5,936,053 | A | 8/1999 | Fukuoka et al. |
| 6,051,727 | A | 4/2000 | Küber et al. ................... 556/11 |
| 6,057,408 | A | 5/2000 | Winter et al. ................. 526/160 |
| 6,136,742 | A | 10/2000 | Chang ........................ 502/108 |
| 6,242,544 | B1 | 6/2001 | Küber et al. ................. 526/127 |
| 6,255,506 | B1 | 7/2001 | Küber et al. ................... 556/11 |
| 6,380,122 | B1 * | 4/2002 | Kuchta et al. ............... 502/103 |
| 6,620,953 | B1 | 9/2003 | Bingel et al. .................. 556/11 |

FOREIGN PATENT DOCUMENTS

| CA | 2191661 | 6/1997 | |
| EP | 0 576 970 | 1/1994 | ........... C07F/17/00 |
| EP | 0 629 632 A | 12/1994 | |
| EP | 0 646 624 A | 4/1995 | |
| EP | 0 704 461 A | 4/1996 | |
| EP | 0 704 463 A | 4/1996 | |
| EP | 0 776 913 A | 6/1997 | |
| EP | 0 816 395 A | 1/1998 | |
| EP | 0 846 696 A | 6/1998 | |
| EP | 0 775 148 B | 8/1999 | |
| WO | WO 98/40331 | 9/1998 | |
| WO | WO 98/40416 | 9/1998 | |
| WO | WO 98/40419 | 9/1998 | |
| WO | WO 99/12943 | 3/1999 | |
| WO | WO 99/33881 | 7/1999 | |
| WO | WO 99/42497 | 8/1999 | |
| WO | WO 00/20462 | 4/2000 | |
| WO | WO 01/48034 A2 | 7/2001 | |

OTHER PUBLICATIONS

D.P. Krut'ko et al., "Synthesis and photoinduced isomerization of ansa–{η[5], η[5]'-[1,1'-(1-silacyclopent-3-ene3-1m, 1-diyl)bis(indenyl)]}–dichlorozirconium. The crystal structure of its meso form"—*Russian Chemical Bulletin* vol. 47 (11), Nov., 1998—pp. 2280–2285.

Woei–Min Tsai et al., "Silolene–Bridged Zirconocenium Polymerization Catalysts" *Journal of Polymer Science, Part A: Polymer Chemistry*, vol. 32, pp. 149–158 (1994).

(Continued)

*Primary Examiner*—Mark L. Bell
*Assistant Examiner*—J. Pasterczyk
(74) *Attorney, Agent, or Firm*—Paige Schmidt

(57) ABSTRACT

This invention relates to bridged indenyl metallocene compositions and their use in the preparation of catalyst systems for olefin polymerization, particularly propylene polymerization. The bridge may be represented by the formula:

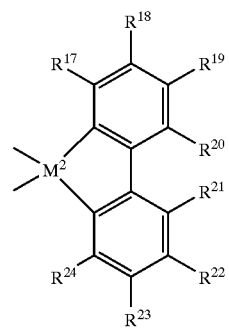

wherein: $R^{17}$ to $R^{24}$ are identical or different, and are one of a hydrogen atom, a $C_1$–$C_{10}$ alkyl group, a $C_1$–$C_{10}$ alkoxy group, a $C_6$–$C_{10}$ aryl group, a $C_6$–$C_{10}$ aryloxy group, a $C_2$–$C_{10}$ alkenyl group, a $C_7$–$C_{40}$ arylalkyl group, a $C_7$–$C_{40}$ alkylaryl group, a $C_8$–$C_{40}$ arylalkenyl group, or a halogen atom, or together are a conjugated diene which is optionally substituted with one or more hydrocarbyl, tri(hydrocarbyl) silyl groups or hydrocarbyl, tri(hydrocarbyl) silylhydrocarbyl groups, said diene having up to 30 atoms not counting hydrogen;

or two or more adjacent radicals $R^{17}$ to $R^{24}$, including $R^{20}$ and $R^{21}$, together with the atoms connecting them form one or more rings; and $M^2$ is carbon, silicon, germanium or tin.

6 Claims, No Drawings

OTHER PUBLICATIONS

U.S. Appl. No. 09/620,359, filed Jul. 19, 2000 (Inventors Mathew C. Kuchta, Udo M. Stehling, Robert T. Li, William T. Haygood, Jr. & Terry J. Burkhardt), entitled "Metallocene Compositions".

U.S. Appl. No. 09/620,341, filed Jul. 19, 2000 (Inventors Mathew C. Kuchta, Udo M. Stehling, Robert T. Li, William T. Haygood, Jr. & Terry J. Burkhardt), entitled "Metallocene Compositions".

U.S. Appl. No. 09/619,751, filed Jul. 19, 2000 (Inventors Mathew C. Kuchta, Udo M. Stehling, Robert T. Li, William T. Haygood, Jr. & Terry J. Burkhardt), entitled "Metallocene Compositions".

U.S. Appl. No. 09/619,757, filed Jul. 19, 2000 (Inventors Mathew C. Kuchta, Udo M. Stehling, Robert T. Li, William T. Haygood, Jr. & Terry J. Burkhardt), entitled "Metallocene Compositions".

U.S. Appl. No. 09/620,613, filed Jul. 19, 2000 (Inventors Mathew C. Kuchta, Udo M. Stehling, Robert T. Li, William T. Haygood, Jr. & Terry J. Burkhardt), entitled "Metallocene Compositions".

U.S. Appl. No. 09/620,175, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions".

U.S. Appl. No. 09/619,759, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions".

U.S. Appl. No. 09/619,748, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions".

U.S. Appl. No. 09/620,304, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions".

U.S. Appl. No. 09/620,522, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions".

U.S. Appl. No. 09/619,752, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions".

U.S. Appl. No. 09/619,750, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions".

U.S. Appl. No. 09/619,749, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions".

U.S. Appl. No. 09/620,303, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions".

U.S. Appl. No. 09/619,764, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions".

U.S. Appl. No. 09/620,302, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions".

U.S. Appl. No. 09/620,198, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions".

Abstract for EP 0 576 970, published Jan. 5, 1994, entitled "Preparation and Olefin Polymerization Catalytic Activity of Aryl Substituted Indenyl Metallocenes".

* cited by examiner

METALLOCENE COMPOSITIONS

This application is a divisional of U.S. patent application Ser. No. 09/620,046, filed Jul. 19, 2000, now U.S. Pat. No. 6,380,122, which is based on U.S. Provisional Patent Application Ser. No. 60/215,597, filed Jun. 30, 2000.

FIELD

This invention relates to metallocene compositions and their use in the preparation of catalyst systems for olefin polymerization, particularly propylene polymerization.

BACKGROUND

The use of metallocene compositions in olefin polymerization is well known. Metallocenes containing substituted, bridged indenyl derivatives are noted for their ability to produce isotactic propylene polymers having high isotacticity and narrow molecular weight distribution. Considerable effort has been made toward obtaining metallocene produced propylene polymers having ever-higher molecular weight and melting point, while maintaining suitable catalyst activity.

Toward this end it has been found that there is a direct relationship between the way in which a metallocene is substituted, and the molecular structure of the resulting polymer. For the substituted, bridged indenyl type metallocenes, it is now well established that the type and arrangement of substituents on the indenyl groups, as well as the type of bridge connecting the indenyl groups, determines such polymer attributes as molecular weight and melting point. Unfortunately, it is impossible at this time to accurately correlate specific substitution or bridging patterns with specific polymer attributes, though trends may be identified.

For example, U.S. Pat. No. 5,840,644 describes certain metallocenes containing aryl-substituted indenyl derivatives as ligands, which are said to provide propylene polymers having high isotacticity, narrow molecular weight distribution and very high molecular weight.

Likewise, U.S. Pat. No. 5,936,053 describes certain metallocene compounds said to be useful for producing high molecular weight propylene polymers. These metallocenes have a specific hydrocarbon substituent at the 2 position and an unsubstituted aryl substituent at the 4 position, on each indenyl group of the metallocene compound.

WO 98/40419 and WO 99/42497 both describe certain supported catalyst systems for producing propylene polymers having high melting point. Metallocene compositions and their activators are often combined with a support material in order to obtain a catalyst system that is less likely to cause reactor fouling. However, it is known that supported metallocene catalyst systems tend to result in a polymer having lower melting point than would otherwise be obtained if the metallocene were not supported.

Much of the current research in this area has been directed toward using metallocene catalyst systems under commercially relevant process conditions, to obtain propylene polymers having melting points higher than known metallocene catalyst systems and close to, or as high as, propylene polymers obtained using conventional, Ziegler-Natta catalyst systems, i.e., 160° C. or higher. The present inventors have discovered metallocene compounds that have this capability.

SUMMARY

The present invention relates generally to metallocene compounds represented by the formula:

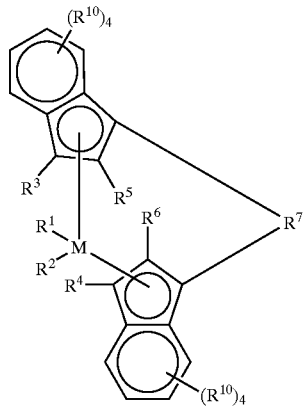

wherein: M is a metal of Group 4, 5, or 6 of the Periodic Table preferably, zirconium, hafnium and titanium, most preferably zirconium;

$R^1$ and $R^2$ are identical or different, preferably identical, and are one of a hydrogen atom, a $C_1$–$C_{10}$ alkyl group, preferably a $C_1$–$C_3$ alkyl group, a $C_1$–$C_{10}$ alkoxy group, preferably a $C_1$–$C_3$ alkoxy group, a $C_6$–$C_{10}$ aryl group, preferably a $C_6$–$C_8$ aryl group, a $C_6$–$C_{10}$ aryloxy group, preferably a $C_6$–$C_8$ aryloxy group, a $C_2$–$C_{10}$ alkenyl group, preferably a $C_2$–$C_4$ alkenyl group, a $C_7$–$C_{40}$ arylalkyl group, preferably a $C_7$–$C_{10}$ arylalkyl group, a $C_7$–$C_{40}$ alkylaryl group, preferably a $C_7$–$C_{12}$ alkylaryl group, a $C_8$–$C_{40}$ arylalkenyl group, preferably a $C_8$–$C_{12}$ arylalkenyl group, or a halogen atom, preferably chlorine; or a conjugated diene which is optionally substituted with one or more hydrocarbyl, tri(hydrocarbyl)silyl groups or hydrocarbyl, tri(hydrocarbyl)silylhydrocarbyl groups, said diene having up to 30 atoms not counting hydrogen;

$R^5$ and $R^6$ are identical or different, preferably identical, are one of a hydrogen atom, a halogen atom, preferably a fluorine, chlorine or bromine atom, a $C_1$–$C_{10}$ alkyl group, preferably a $C_1$–$C_4$ alkyl group, which may be halogenated, a $C_6$–$C_{10}$ aryl group, which may be halogenated, preferably a $C_6$–$C_8$ aryl group, a $C_2$–$C_{10}$ alkenyl group, preferably a $C_2$–$C_4$ alkenyl group, a $C_7$–$C_{40}$ arylalkyl group, preferably a $C_7$–$C_{10}$ arylalkyl group, a $C_7$–$C_{40}$ alkylaryl group, preferably a $C_7$–$C_{12}$ alkylaryl group, a $C_8$–$C_{40}$ arylalkenyl group, preferably a $C_8$–$C_{12}$ arylalkenyl group, a —$NR_2^{15}$, —$SR^{15}$, —$OR^{15}$, —$OSiR_3^{15}$ or —$PR_2^{15}$ radical, wherein: $R^{15}$ is one of a halogen atom, preferably a chlorine atom, a $C_1$–$C_{10}$ alkyl group, preferably a $C_1$–$C_3$ alkyl group, or a $C_6$–$C_{10}$ aryl group, preferably a $C_6$–$C_9$ aryl group;

$R^7$ is

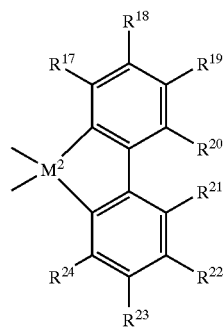

wherein:

$R^{17}$ to $R^{24}$ are as defined for $R^1$ and $R^2$, or two or more adjacent radicals $R^{17}$ to $R^{24}$, including $R^{20}$ and $R^{21}$, together with the atoms connecting them form one or more rings;

$M^2$ is carbon, silicon, germanium or tin;

the radicals $R^3$, $R^4$, and $R^{10}$ are identical or different and have the meanings stated for $R^5$ and $R^6$, or two adjacent $R^{10}$ radicals are joined together to form a ring, preferably a ring containing from about 4–6 carbon atoms.

More specifically, the present invention relates generally to metallocene compounds represented by the formula:

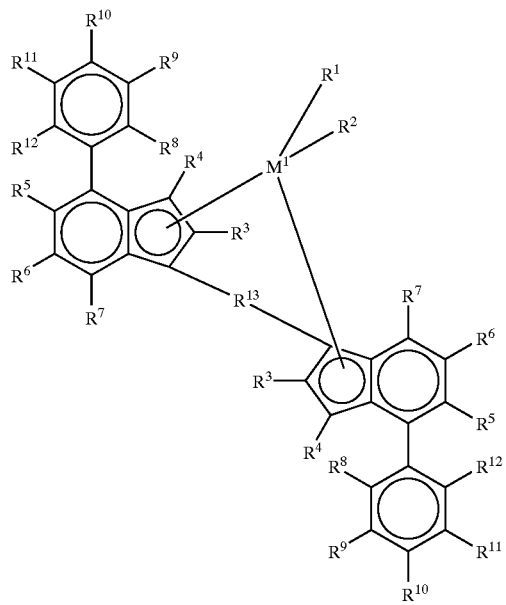

(I)

wherein: $M^1$ is selected from the group consisting of titanium, zirconium, hafnium, vanadium, niobium, tantalum, chromium, molybdenum and tungsten;

$R^1$ and $R^2$ are identical or different, and are one of a hydrogen atom, a $C_1$–$C_{10}$ alkyl group, a $C_1$–$C_{10}$ alkoxy group, a $C_6$–$C_{10}$ aryl group, a $C_6$–$C_{10}$ aryloxy group, a $C_2$–$C_{10}$ alkenyl group, a $C_2$–$C_{40}$ alkenyl group, a $C_7$–$C_{40}$ arylalkyl group, a $C_7$–$C_{40}$ alkylaryl group, a $C_8$–$C_{40}$ arylalkenyl group, an OH group or a halogen atom; or a conjugated diene which is optionally substituted with one or more hydrocarbyl, tri(hydrocarbyl)silyl groups or hydrocarbyl, tri(hydrocarbyl)silylhydrocarbyl groups, said diene having up to 30 atoms not counting hydrogen;

$R^3$ are identical or different and are each a hydrogen atom, a halogen atom, a $C_1$–$C_{10}$ alkyl group which may be halogenated, a $C_6$–$C_{10}$ aryl group which may be halogenated, a $C_2$–$C_{10}$ alkenyl group, a $C_7$–$C_{40}$-arylalkyl group, a $C_7$–$C_{40}$ alkylaryl group, a $C_8$–$C_{40}$ arylalkenyl group, a —NR'$_2$, —SR', —OR', —OSiR'$_3$ or —PR'$_2$ radical, wherein: R' is one of a halogen atom, a $C_1$–$C_{10}$ alkyl group, or a $C_6$–$C_{10}$ aryl group;

$R^4$ to $R^7$ are identical or different and are hydrogen, as defined for $R^3$ or two or more adjacent radicals $R^5$ to $R^7$ together with the atoms connecting them form one or more rings;

$R^{13}$ is represented by the formula:

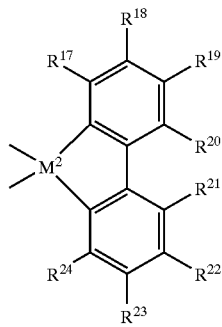

wherein: $R^{17}$ to $R^{24}$ are as defined for $R^1$ and $R^2$, or two or more adjacent radicals $R^{17}$ to $R^{24}$, including $R^{20}$ and $R^{21}$, together with the atoms connecting them form one or more rings;

$M^2$ is carbon, silicon, germanium or tin;

$R^8$, $R^9$, $R^{10}$ $R^{11}$ and $R^{12}$ are identical or different and have the meanings stated for $R^4$ to $R^7$.

The present invention further relates to metallocene catalyst systems comprising one or more or the above compounds and one or more activators or cocatalysts, and optionally, support material, and to the use of such metallocene catalyst systems in olefin polymerization, particularly propylene polymer polymerization.

DESCRIPTION

In one embodiment, the metallocenes of the present invention may be represented by the formula:

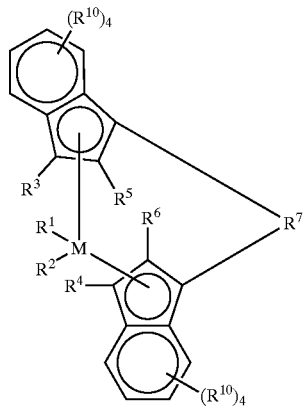

wherein: M is a metal of Group 4, 5, or 6 of the Periodic Table preferably, zirconium, hafnium and titanium, most preferably zirconium;

$R^1$ and $R^2$ are identical or different, preferably identical, and are one of a hydrogen atom, a $C_1$–$C_{10}$ alkyl group, preferably a $C_1$–$C_3$ alkyl group, a $C_1$–$C_{10}$ alkoxy group, preferably a $C_1$–$C_3$ alkoxy group, a $C_6$–$C_{10}$ aryl group, preferably a $C_6$–$C_8$ aryl group, a $C_6$–$C_{10}$ aryloxy group, preferably a $C_6$–$C_8$ aryloxy group, a $C_2$–$C_{10}$ alkenyl group, preferably a $C_2$–$C_4$ alkenyl group, a $C_7$–$C_{40}$ arylalkyl group, preferably a $C_7$–$C_{10}$ arylalkyl group, a $C_7$–$C_{40}$ alkylaryl group, preferably a $C_7$–$C_{12}$ alkylaryl group, a $C_8$–$C_{40}$ arylalkenyl group, preferably a $C_8$–$C_{12}$ arylalkenyl group, or a halogen atom, preferably chlorine; $R^1$ and $R^2$ may also be joined together to form an alkanediyl group or a conjugated $C_{4-40}$ diene ligand which is coordinated to $M^1$ in a metallocyclopentene fashion; $R^1$ and $R^2$ may also be identical or different conjugated dienes, optionally substituted with one or more hydrocarbyl, tri(hydrocarbyl)silyl groups or hydrocarbyl, tri(hydrocarbyl)silylhydrocarbyl groups, said dienes having up to 30 atoms not counting hydrogen and forming a π complex with M, examples include, but are not limited to: 1,4-diphenyl-1,3-butadiene, 1,3-pentadiene, 2-methyl-1,3-pentadiene, 2,4-hexadiene, 1-phenyl-1,3-pentadiene, 1,4-dibenzyl-1,3-butadiene, 1,4-ditolyl-1,3-butadiene, 1,4-bis(trimethylsilyl)-1,3-butadiene, and 1,4-dinaphthyl-1,3-butadiene.

$R^5$ and $R^6$ are identical or different, preferably identical, are one of a hydrogen atom, a halogen atom, preferably a fluorine, chlorine or bromine atom, a $C_1$–$C_{10}$ alkyl group, preferably a $C_1$–$C_4$ alkyl group, which may be halogenated, a $C_6$–$C_{10}$ aryl group, which may be halogenated, preferably a $C_6$–$C_8$ aryl group, a $C_2$–$C_{10}$ alkenyl group, preferably a $C_2$–$C_4$ alkenyl group, a $C_7$–$C_{40}$-arylalkyl group, preferably a $C_7$–$C_{10}$ arylalkyl group, a $C_7$–$C_{40}$ alkylaryl group, preferably a $C_7$–$C_{12}$ alkylaryl group, a $C_8$–$C_{40}$ arylalkenyl group, preferably a $C_8$–$C_{12}$ arylalkenyl group, a —$NR_2^{15}$, —$SR^{15}$, —$OR^{15}$, —$OSiR_3^{15}$ or —$PR_2^{15}$ radical, wherein: $R^{15}$ is one of a halogen atom, preferably a chlorine atom, a $C_1$–$C_{10}$ alkyl group, preferably a $C_1$–$C_3$ alkyl group, or a $C_6$–$C_{10}$ aryl group, preferably a $C_6$–$C_9$ aryl group;

$R^7$ is

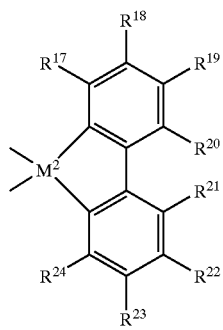

wherein:

$R^{17}$ to $R^{24}$ are as defined for $R^1$ and $R^2$, or two or more adjacent radicals $R^{17}$ to $R^{24}$, including $R^{20}$ and $R^{21}$, together with the atoms connecting them form one or more rings;

$M^2$ is carbon, silicon, germanium or tin; and the radicals $R^3$, $R^4$, and $R^{10}$ are identical or different and have the meanings stated for $R^5$ and $R^6$, or two adjacent $R^{10}$ radicals are joined together to form a ring, preferably a ring containing from about 4–6 carbon atoms.

Particularly preferred metallocenes of the present invention are represented by the formula:

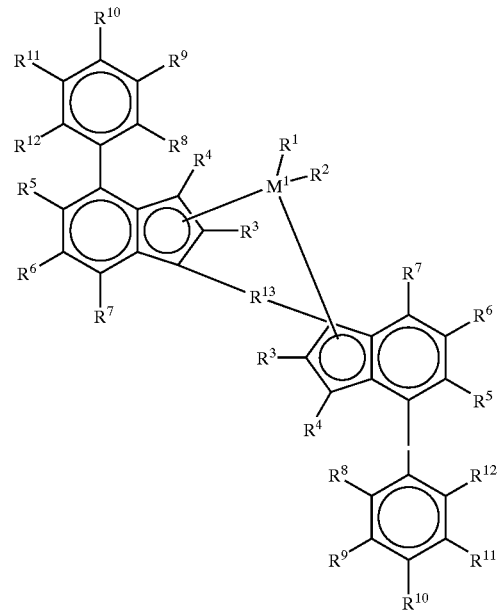

(I)

wherein: $M^1$ is selected from the group consisting of titanium, zirconium, hafnium, vanadium, niobium, tantalum, chromium, molybdenum and tungsten, preferably zirconium, hafnium or titanium, most preferably zirconium;

$R^1$ and $R^2$ are identical or different, and are one of a hydrogen atom, a $C_1$–$C_{10}$ alkyl group, a $C_1$–$C_{10}$ alkoxy group, a $C_6$–$C_{10}$ aryl group, a $C_6$–$C_{10}$ aryloxy group, a $C_2$–$C_{10}$ alkenyl group, a $C_2$–$C_{40}$ alkenyl group, a $C_7$–$C_{40}$ arylalkyl group, a $C_7$–$C_{40}$ alkylaryl group, a $C_8$–$C_{40}$ arylalkenyl group, an OH group or a halogen atom, or are a conjugated diene which is optionally substituted with one or more hydrocarbyl, tri(hydrocarbyl)silyl groups or hydrocarbyl, tri(hydrocarbyl)silylhydrocarbyl groups, said diene having up to 30 atoms not counting hydrogen;

preferably $R^1$ and $R^2$ are identical and are a $C_1$–$C_3$ alkyl or alkoxy group, a $C_6$–$C_8$ aryl or aryloxy group, a $C_2$–$C_4$ alkenyl group, a $C_7$–$C_{10}$ arylalkyl group, a $C_7$–$C_{12}$ alkylaryl group, or a halogen atom, preferably chlorine;

$R^3$ are identical or different and are each a hydrogen atom, a halogen atom, a $C_1$–$C_{10}$ alkyl group which may be halogenated, a $C_6$–$C_{10}$ aryl group which may be halogenated, a $C_2$–$C_{10}$ alkenyl group, a $C_7$–$C_{40}$-arylalkyl group, a $C_7$–$C_{40}$ alkylaryl group, a $C_8$–$C_{40}$ arylalkenyl group, a —$NR'_2$, —$SR'$, —$OR'$, —$OSiR'_3$ or —$PR'_2$ radical, wherein: $R'$ is one of a halogen atom, a $C_1$–$C_{10}$ alkyl group, or a $C_6$–$C_{10}$ aryl group; preferably $R^3$ is not a hydrogen atom;

preferably each $R^3$ is identical and is a fluorine, chlorine or bromine, atom, a $C_1$–$C_4$ alkyl group which may be halogenated, a $C_6$–$C_8$ aryl group which may be halogenated, a —$NR'_2$, —$SR'$, —$OR'$, —$OSiR'_3$ or —$PR'_2$ radical, wherein: $R'$ is one of a chlorine atom, a $C_1$–$C_4$ alkyl group, or a $C_6$–$C_8$ aryl group;

$R^4$ to $R^7$ are identical or different and are hydrogen, as defined for $R^3$ or two or more adjacent radicals $R^5$ to $R^7$ together with the atoms connecting them form one or more rings;

$R^{13}$ is represented by the formula:

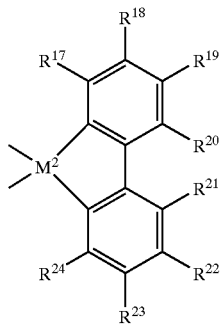

wherein: $R^{17}$ to $R^{24}$ are as defined for $R^1$ and $R^2$, or two or more adjacent radicals $R^{17}$ to $R^{24}$, including $R^{20}$ and $R^{21}$, together with the atoms connecting them form one or more rings; preferably, $R^{17}$ to $R^{24}$ are hydrogen.

$M^2$ is carbon, silicon, germanium or tin, preferably silicon; and $R^8$, $R^9$, $R^{10}$, $R^{11}$ and $R^{12}$ are identical or different and have the meanings stated for $R^4$ to $R^7$.

As utilized herein, the term "alkyl", alone or in combination, means a straight-chain or branched-chain alkyl radical. Examples of such radicals include, but are not limited to, methyl, ethyl, n-propyl, isopropyl, n-butyl, isobutyl, sec-butyl, tert-butyl, pentyl, iso-amyl, hexyl, octyl and the like. The term "alkenyl" means a straight-chain or branched-chain hydrocarbon radical having one or more double bonds. Examples of suitable alkenyl radicals include, but are not limited to, ethenyl, propenyl, allyl, 1,4-butadienyl and the like. The term "alkoxy" means an alkyl ether radical wherein: the term alkyl is as defined above. Examples of suitable alkyl ether radicals include, but are not limited to, methoxy, ethoxy, n-propoxy, isopropoxy, n-butoxy, iso-butoxy, sec-butoxy, tert-butoxy and the like. The term "aryl" means a phenyl, azulenyl, or naphthyl radical and the like which optionally contains a heteroatom and/or carries one or more substituents, for example, alkyl, alkoxy, halogen, hydroxy, amino, nitro etc.

The following are particularly preferred metallocenes:

rac-9-silafluorendiyl(2-methyl-4-phenylindenyl)$_2$zirconium dichloride;
rac-9-silafluorendiyl(2-ethyl-4-phenylindenyl)$_2$zirconium dichloride;
rac-9-silafluorendiyl(2-n-propyl-4-phenylindenyl)$_2$zirconium dichloride;
rac-9-silafluorendiyl(2-iso-propyl-4-phenylindenyl)$_2$zirconium dichloride;
rac-9-silafluorendiyl(2-n-butyl-4-phenylindenyl)$_2$zirconium dichloride;
rac-9-silafluorendiyl(2-iso-butyl-4-phenylindenyl)$_2$zirconium dichloride;
rac-9-silafluorendiyl(2-sec-butyl-4-phenylindenyl)$_2$zirconium dichloride;
rac-9-silafluorendiyl(2-tert-butyl-4-phenylindenyl)$_2$zirconium dichloride;
rac-9-silafluorendiyl(2-methyl-4-phenylindenyl)$_2$hafnium dichloride;
rac-9-silafluorendiyl(2-ethyl-4-phenylindenyl)$_2$hafnium dichloride;
rac-9-silafluorendiyl(2-n-propyl-4-phenylindenyl)$_2$hafnium dichloride;
rac-9-silafluorendiyl(2-iso-propyl-4-phenylindenyl)$_2$hafnium dichloride;
rac-9-silafluorendiyl(2-n-butyl-4-phenylindenyl)$_2$hafnium dichloride;
rac-9-silafluorendiyl(2-iso-butyl-4-phenylindenyl)$_2$hafnium dichloride;
rac-9-silafluorendiyl(2-sec-butyl-4-phenylindenyl)$_2$hafnium dichloride;
rac-9-silafluorendiyl(2-tert-butyl-4-phenylindenyl)$_2$hafnium dichloride;
rac-9-silafluorendiyl(2-methyl-4-phenylindenyl)$_2$zirconium dimethyl;
rac-9-silafluorendiyl(2-ethyl-4-phenylindenyl)$_2$zirconium diethyl;
rac-9-silafluorendiyl(2-n-propyl-4-phenylindenyl)$_2$zirconium dimethyl;
rac-9-silafluorendiyl(2-iso-propyl-4-phenylindenyl)$_2$zirconium dimethyl;
rac-9-silafluorendiyl(2-n-butyl-4-phenylindenyl)$_2$zirconium dimethyl;
rac-9-silafluorendiyl(2-iso-butyl-4phenylindenyl)$_2$zirconium dimethyl;
rac-9-silafluorendiyl(2-sec-butyl-4-phenylindenyl)$_2$zirconium dimethyl;
rac-9-silafluorendiyl(2-tert-butyl-4-phenylindenyl)$_2$zirconium dimethyl;
rac-9-silafluorendiyl(2-methyl-4-phenylindenyl)$_2$hafnium dimethyl;
rac-9-silafluorendiyl(2-ethyl-4-phenylindenyl)$_2$hafnium dimethyl;
rac-9-silafluorendiyl(2-n-propyl-4-phenylindenyl)$_2$hafnium dimethyl;
rac-9-silafluorendiyl(2-iso-propyl-4-phenylindenyl)$_2$hafnium dimethyl;
rac-9-silafluorendiyl(2-n-butyl-4-phenylindenyl)$_2$hafnium dimethyl;
rac-9-silafluorendiyl(2-iso-butyl-4-phenylindenyl)$_2$hafnium dimethyl;
rac-9-silafluorendiyl(2-sec-butyl-4-phenylindenyl)$_2$hafnium dimethyl;
rac-9-silafluorendiyl(2-tert-butyl-4-phenylindenyl)$_2$hafnium dimethyl;
rac-9-silafluorendiyl(2-methyl, 4-[3',5'-di-tbutylphenyl] indenyl)$_2$zirconium dichloride;
rac-9-silafluorendiyl(2-ethyl, 4-[3',5'-di-tbutylphenyl] indenyl)$_2$zirconium dichloride;
rac-9-silafluorendiyl(2-n-propyl, 4-[3',5'-di-tbutylphenyl] indenyl)$_2$zirconium dichloride;
rac-9-silafluorendiyl(2-iso-propyl, 4-[3',5'-di-tbutylphenyl] indenyl)$_2$zirconium dichloride;
rac-9-silafluorendiyl(2-n-butyl, 4-[3',5'-di-tbutylphenyl] indenyl)$_2$zirconium dichloride;
rac-9-silafluorendiyl(2-iso-butyl, 4-[3',5'-di-tbutylphenyl] indenyl)$_2$zirconium dichloride;
rac-9-silafluorendiyl(2-sec-butyl, 4-[3',5'-di-tbutylphenyl] indenyl)$_2$zirconium dichloride;
rac-9-silafluorendiyl(2-tert-butyl, 4-[3',5'-di-tbutylphenyl] indenyl)$_2$zirconium dichloride;
rac-9-silafluorendiyl(2-methyl, 4-[3',5'-di-tbutylphenyl] indenyl)$_2$hafnium dichloride;
rac-9-silafluorendiyl(2-ethyl, 4-[3',5'-di-tbutylphenyl] indenyl)$_2$hafnium dichloride;
rac-9-silafluorendiyl(2-n-propyl, 4-[3',5'-di-tbutylphenyl] indenyl)$_2$hafnium dichloride;
rac-9-silafluorendiyl(2-iso-propyl, 4-[3',5'-di-tbutylphenyl] indenyl)$_2$hafnium dichloride;
rac-9-silafluorendiyl(2-n-butyl, 4-[3',5'-di-tbutylphenyl] indenyl)$_2$hafnium dichloride;
rac-9-silafluorendiyl(2-iso-butyl, 4-[3',5'-di-tbutylphenyl] indenyl)$_2$hafnium dichloride;
rac-9-silafluorendiyl(2-sec-butyl, 4-[3',5'-di-tbutylphenyl] indenyl)$_2$hafnium dichloride;
rac-9-silafluorendiyl(2-tert-butyl, 4-[3',5'-di-tbutylphenyl] indenyl)$_2$hafnium dichloride;
rac-9-silafluorendiyl(2-methyl, 4-[3',5'-di-tbutylphenyl] indenyl)$_2$zirconium dimethyl;

rac-9-silafluorendiyl(2-ethyl, 4-[3',5'-di-tbutylphenyl]indenyl)₂zirconium dimethyl;
rac-9-silafluorendiyl(2-n-propyl, 4-[3',5'-di-tbutylphenyl]indenyl)₂zirconium dimethyl;
rac-9-silafluorendiyl(2-iso-propyl, 4-[3',5'-di-tbutylphenyl]indenyl)₂zirconium dimethyl;
rac-9-silafluorendiyl(2-n-butyl, 4-[3',5'-di-tbutylphenyl]indenyl)₂zirconium dimethyl;
rac-9-silafluorendiyl(2-iso-butyl, 4-[3',5'-di-tbutylphenyl]indenyl)₂zirconium dimethyl;
rac-9-silafluorendiyl(2-sec-butyl, 4-[3',5'-di-tbutylphenyl]indenyl)₂zirconium dimethyl;
rac-9-silafluorendiyl(2-tert-butyl, 4-[3',5'-di-tbutylphenyl]indenyl)₂zirconium dimethyl;
rac-9-silafluorendiyl(2-methyl, 4-[3',5'-di-tbutylphenyl]indenyl)₂hafnium dimethyl;
rac-9-silafluorendiyl(2-ethyl, 4-[3',5'-di-tbutylphenyl]indenyl)₂hafnium dimethyl;
rac-9-silafluorendiyl(2-n-propyl, 4-[3',5'-di-tbutylphenyl]indenyl)₂hafnium dimethyl;
rac-9-silafluorendiyl(2-iso-propyl, 4-[3',5'-di-tbutylphenyl]indenyl)₂hafnium dimethyl;
rac-9-silafluorendiyl(2-n-butyl, 4-[3',5'-di-tbutylphenyl]indenyl)₂hafnium dimethyl;
rac-9-silafluorendiyl(2-iso-butyl, 4-[3',5'-di-tbutylphenyl]indenyl)₂hafnium dimethyl;
rac-9-silafluorendiyl(2-sec-butyl, 4-[3',5'-di-tbutylphenyl]indenyl)₂hafnium dimethyl;
rac-9-silafluorendiyl(2-tert-butyl, 4-[3',5'-di-tbutylphenyl]indenyl)₂hafnium dimethyl;
rac-9-silafluorendiyl(2-methyl, 4-[3',5'-bis-trifluoromethylphenyl]indenyl)₂zirconium dichloride;
rac-dimethylsiladiyl(2-ethyl, 4-[3',5'-bis-trifluoromethylphenyl]indenyl)₂zirconium dichloride;
rac-9-silafluorendiyl(2-n-propyl, 4-[3',5'-bis-trifluoromethylphenyl]indenyl)₂zirconium dichloride;
rac-9-silafluorendiyl(2-iso-propyl, 4-[3',5'-bis-trifluoromethylphenyl]indenyl)₂zirconium dichloride;
rac-9-silafluorendiyl(2-n-butyl, 4-[3',5'-bis-trifluoromethylphenyl]indenyl)₂zirconium dichloride;
rac-9-silafluorendiyl(2-iso-butyl, 4-[3',5'-bis-trifluoromethylphenyl]indenyl)₂zirconium dichloride;
rac-9-silafluorendiyl(2-sec-butyl, 4-[3',5'-bis-trifluoromethylphenyl]indenyl)₂zirconium dichloride;
rac-9-silafluorendiyl(2-tert-butyl, 4-[3',5'-bis-trifluoromethylphenyl]indenyl)₂zirconium dichloride;
rac-9-silafluorendiyl(2-methyl, 4-[3',5'-bis-trifluoromethylphenyl]indenyl)₂hafnium dichloride;
rac-9-silafluorendiyl(2-ethyl, 4-[3',5'-bis-trifluoromethylphenyl]indenyl)₂hafnium dichloride;
rac-9-silafluorendiyl(2-n-propyl, 4-[3',5'-bis-trifluoromethylphenyl]indenyl)₂hafnium dichloride;
rac-9-silafluorendiyl(2-iso-propyl, 4-[3',5'-bis-trifluoromethylphenyl]indenyl)₂hafnium dichloride;
rac-9-silafluorendiyl(2-n-butyl, 4-[3',5'-bis-trifluoromethylphenyl]indenyl)₂hafnium dichloride;
rac-9-silafluorendiyl(2-iso-butyl, 4-[3',5'-bis-trifluoromethylphenyl]indenyl)₂hafnium dichloride;
rac-9-silafluorendiyl(2-sec-butyl, 4-[3',5'-bis-trifluoromethylphenyl]indenyl)₂hafnium dichloride;
rac-9-silafluorendiyl(2-tert-butyl, 4-[3',5'-bis-trifluoromethylphenyl]indenyl)₂hafnium dichloride;
rac-9-silafluorendiyl(2-methyl, 4-[3',5'-bis-trifluoromethylphenyl]indenyl)₂zirconium dimethyl;
rac-9-silafluorendiyl(2-n-propyl, 4-[,3',5'-bis-trifluoromethylphenyl]indenyl)₂zirconium dimethyl;
rac-9-silafluorendiyl(2-iso-propyl, 4-[3',5'-bis-trifluoromethylphenyl]indenyl)₂zirconium dimethyl;
rac-9-silafluorendiyl(2-n-butyl, 4-[3',5'-bis-trifluoromethylphenyl]indenyl)₂zirconium dimethyl;
rac-9-silafluorendiyl(2-iso-butyl, 4-[3',5'-bis-trifluoromethylphenyl]indenyl)₂zirconium dimethyl;
rac-9-silafluorendiyl(2-sec-butyl, 4-[3',5'-bis-trifluoromethylphenyl]indenyl)₂zirconium dimethyl;
rac-9-silafluorendiyl(2-tert-butyl, 4-[3',5'-bis-trifluoromethylphenyl]indenyl)₂zirconium dimethyl;
rac-9-silafluorendiyl(2-methyl, 4-[3',5'-bis-trifluoromethylphenyl]indenyl)₂hafnium dimethyl;
rac-9-silafluorendiyl(2-ethyl, 4-[3',5'-bis-trifluoromethylphenyl]indenyl)₂hafnium dimethyl;
rac-9-silafluorendiyl(2-n-propyl, 4-[3',5'-bis-trifluoromethylphenyl]indenyl)₂hafnium dimethyl;
rac-9-silafluorendiyl(2-iso-propyl, 4-[3',5'-bis-trifluoromethylphenyl]indenyl)₂hafnium dimethyl;
rac-9-silafluorendiyl(2-n-butyl, 4-[3',5'-bis-trifluoromethylphenyl]indenyl)₂hafnium dimethyl;
rac-9-silafluorendiyl(2-iso-butyl, 4-[3',5'-bis-trifluoromethylphenyl]indenyl)₂hafnium dimethyl;
rac-9-silafluorendiyl(2-sec-butyl, 4-[3',5'-bis-trifluoromethylphenyl]indenyl)₂hafnium dimethyl
rac-9-silafluorendiyl(2-tert-butyl, 4-[3',5'-bis-trifluoromethylphenyl]indenyl)₂hafnium dimethyl;
rac-9-silafluorendiyl(2-methyl, 4-[3',5'-di-iso-propylphenyl]indenyl)₂zirconium dichloride;
rac-9-silafluorendiyl(2-ethyl, 4-[3',5'-di-iso-propylphenyl]indenyl)₂zirconium dichloride;
rac-9-silafluorendiyl(2-n-propyl, 4-[3',5'-di-iso-propylphenyl]indenyl)₂zirconium dichloride;
rac-9-silafluorendiyl(2-iso-propyl, 4-[3',5'-di-iso-propylphenyl]indenyl)₂zirconium dichloride;
rac-9-silafluorendiyl(2-n-butyl, 4-[3',5'-di-iso-propylphenyl]indenyl)₂zirconium dichloride;
rac-9-silafluorendiyl(2-iso-butyl, 4-[3',5'-di-iso-propylphenyl]indenyl)₂zirconium dichloride;
rac-9-silafluorendiyl(2-sec-butyl, 4-[3',5'-di-iso-propylphenyl]indenyl)₂zirconium dichloride;
rac-9-silafluorendiyl(2tert-butyl, 4-[3',5'-di-iso-propylphenyl]indenyl)₂zirconium dichloride;
rac-9-silafluorendiyl(2-methyl, 4-[3',5'-di-iso-propylphenyl]indenyl)₂hafnium dichloride;
rac-9-silafluorendiyl(2-ethyl, 4-[3',5'-di-iso-propylphenyl]indenyl)₂hafnium dichloride;
rac-9-silafluorendiyl(2-n-propyl, 4-[3',5'-di-iso-propylphenyl]indenyl)₂hafnium dichloride;
rac-9-silafluorendiyl(2-so-propyl, 4-[3',5'-di-iso-propylphenyl]indenyl)₂hafnium dichloride;
rac-9-silafluorendiyl(2-n-butyl, 4-[3',5'-di-iso-propylphenyl]indenyl)₂hafnium dichloride;
rac-9-silafluorendiyl(2-iso-butyl, 4-[3',5'-di-iso-propylphenyl]indenyl)₂hafnium dichloride;
rac-9-silafluorendiyl(2-sec-butyl, 4-[3',5'-di-iso-propylphenyl]indenyl)₂hafnium dichloride;
rac-9-silafluorendiyl(2-tert-butyl, 4-[3',5'-di-iso-propylphenyl]indenyl)₂hafnium dichloride;
rac-9-silafluorendiyl(2-methyl, 4-[3',5'-di-iso-propylphenyl]indenyl)₂zirconium dimethyl;
rac-9-silafluorendiyl(2-ethyl, 4-[3',5'-di-iso-propylphenyl]indenyl)₂zirconium dimethyl;
rac-9-silafluorendiyl(2-n-propyl, 4-[3',5'-di-iso-propylphenyl]indenyl)₂zirconium dimethyl;
rac-9-silafluorendiyl(2-iso-propyl, 4-[3',5'-di-iso-propylphenyl]indenyl)₂zirconium dimethyl;
rac-9-silafluorendiyl(2-n-butyl, 4-[3',5'-di-iso-propylphenyl]indenyl)₂zirconium dimethyl;
rac-9-silafluorendiyl(2-iso-butyl, 4-[3',5'-di-iso-propylphenyl]indenyl)₂zirconium dimethyl;
rac-9-silafluorendiyl(2-sec-butyl, 4-[3',5'-di-iso-propylphenyl]indenyl)₂zirconium dimethyl;
rac-9-silafluorendiyl(2-tert-butyl, 4-[3',5'-di-iso-propylphenyl]indenyl)₂zirconium dimethyl;
rac-9-silafluorendiyl(2-methyl, 4-[3',5'-di-iso-propylphenyl]indenyl)₂zirconium dimethyl;
rac-9-silafluorendiyl(2-ethyl, 4-[3',5'-di-iso-propylphenyl]indenyl)₂hafnium dimethyl;

rac-9-silafluorendiyl(2-n-propyl, 4-[3',5'-di-iso-propylphenyl]indenyl)₂hafnium dimethyl;
rac-9-silafluorendiyl(2-iso-propyl, 4-[3',5'-di-iso-propylphenyl]indenyl)₂hafnium dimethyl;
rac-9-silafluorendiyl(2-n-butyl, 4-[3',5'-di-iso-propylphenyl]indenyl)₂hafnium dimethyl;
rac-9-silafluorendiyl(2-iso-butyl, 4-[3',5'-di-iso-propylphenyl]indenyl)₂hafnium dimethyl;
rac-9-silafluorendiyl(2-sec-butyl, 4-[3',5'-di-iso-propylphenyl]indenyl)₂hafnium dimethyl;
rac-9-silafluorendiyl(2-tert-butyl, 4-[3',5'-di-iso-propylphenyl]indenyl)₂hafnium dimethyl;
rac-9-silafluorendiyl(2-methyl, 4-[3',5'-di-phenylphenyl] indenyl)₂zirconium dichloride;
rac-9-silafluorendiyl(2-ethyl, 4-[3',5'-di-phenylphenyl] indenyl)₂zirconium dichloride;
rac-9-silafluorendiyl(2-n-propyl, 4-[3',5'-di-phenylphenyl] indenyl)₂zirconium dichloride;
rac-9-silafluorendiyl(2-iso-propyl, 4-[3',5'-di-phenylphenyl] indenyl)₂zirconium dichloride;
rac-9-silafluorendiyl(2-n-butyl, 4-[3',5'-di-phenylphenyl] indenyl)₂zirconium dichloride;
rac-9-silafluorendiyl(2-iso-butyl, 4-[3',5'-di-phenylphenyl] indenyl)₂zirconium dichloride;
rac-9-silafluorendiyl(2-tert-butyl, 4-[3',5'-di-phenylphenyl] indenyl)₂zirconium dichloride;
rac-9-silafluorendiyl(2-sec-butyl, 4-[3',5'-di-phenylphenyl] indenyl)₂zirconium dichloride;
rac-9-silafluorendiyl(2-methyl, 4-[, 3',5'-di-phenylphenyl] indenyl)₂hafnium dichloride;
rac-9-silafluorendiyl(2-ethyl, 4-[3',5'-di-phenylphenyl] indenyl)₂hafnium dichloride;
rac-9-silafluorendiyl(2-n-propyl, 4-[3',5'-di-phenylphenyl] indenyl)₂hafnium dichloride;
rac-9-silafluorendiyl(2iso-propyl, 4-[3',5'-di-phenylphenyl] indenyl)₂hafnium dichloride;
rac-9-silafluorendiyl(2-n-butyl, 4-[3',5'-di-phenylphenyl] indenyl)₂hafnium dichloride;
rac-9-silafluorendiyl(2-iso-butyl, 4-[3',5'-di-phenylphenyl] indenyl)₂hafnium dichloride;
rac-9-silafluorendiyl(2-sec-butyl, 4-[3',5'-di-phenylphenyl] indenyl)₂hafnium dichloride;
rac-9-silafluorendiyl(2-tert-butyl, 4-[3',5'-di-phenylphenyl] indenyl)₂hafnium dichloride;
rac-9-silafluorendiyl(2-methyl, 4-[3',5'-di-phenylphenyl] indenyl)₂zirconium dimethyl;
rac-9-silafluorendiyl(2-ethyl, 4-[3',5'-di-phenylphenyl] indenyl)₂zirconium dimethyl;
rac-9-silafluorendiyl(2-n-propyl, 4-[3',5'-di-phenylphenyl] indenyl)₂zirconium dimethyl;
rac-9-silafluorendiyl(2-iso-propyl, 4-[3',5'-di-phenylphenyl] indenyl)₂zirconium dimethyl;
rac-9-silafluorendiyl(2-n-butyl, 4-[3',5'-di-phenylphenyl] indenyl)zirconium dimethyl;
rac-9-silafluorendiyl(2-iso-butyl, 4-[3',5'-di-phenylphenyl] indenyl)₂zirconium dimethyl;
rac-9-silafluorendiyl(2-sec-butyl, 4-[3',5'-di-phenylphenyl] indenyl)₂zirconium dimethyl;
rac-9-silafluorendiyl(2-tert-butyl, 4-[3',5'-di-phenylphenyl] indenyl)₂zirconium dimethyl;
rac-9-silafluorendiyl(2-methyl, 4-[3',5'-di-phenylphenyl] indenyl)₂hafnium dimethyl;
rac-9-silafluorendiyl(2-ethyl, 4-[3',5'di-phenylphenyl] indenyl)₂hafnium dichloride;
rac-9-silafluorendiyl(2-propyl, 4-[3',5'-di-phenylphenyl] indenyl)₂hafnium dimethyl;
rac-9-silafluorendiyl(2-isopropyl, 4-[3',5'-di-phenylphenyl] indenyl)₂hafnium dimethyl;
rac-9-silafluorendiyl(2-butyl, 4-[3',5'-di-phenylphenyl] indenyl)₂hafnium dimethyl;
rac-9-silafluorendiyl(2-methyl, 4-[3',5'-di-tbutylphenyl] indenyl)₂zirconium η⁴-1,4-diphenyl-1,3-butadiene;
rac-9-silafluorendiyl(2-ethyl, 4-[3',5'-di-tbutylphenyl] indenyl)₂zirconium η⁴-1,4-diphenyl-1,3-butadiene;
rac-9-silafluorendiyl(2-propyl, 4-[3',5'-di-tbutylphenyl] indenyl)₂zirconium η⁴-1,4-diphenyl 1,3-butadiene;
rac-9-silafluorendiyl(2-iso-propyl, 4-[3',5'-di-tbutylphenyl] indenyl)₂zirconium η⁴-1,4-diphenyl-1,3-butadiene;
rac-9-silafluorendiyl(2-n-butyl, 4-[3',5'-di-tbutylphenyl] indenyl)₂zirconium η⁴-1,4-diphenyl-1,3-butadiene;
rac-9-silafluorendiyl(2-iso-butyl, 4-[3',5'-di-tbutylphenyl] indenyl)₂zirconium dichloride;
rac-9-silafluorendiyl(2-sec-butyl, 4-[3',5-di-tbutylphenyl] indenyl)₂zirconium η⁴-1,4-diphenyl-1,3-butadiene;
rac-9-silafluorendiyl(2-tert-butyl, 4-[3',5'-di-tbutylphenyl] indenyl)₂zirconium η⁴-1,4-diphenyl-1,3-butadiene;
rac-9-silafluorendiyl(2-methyl, 4-[3',5'-bis-trifluoromethylphenyl]indenyl)₂zirconium η⁴-1,4-diphenyl-1,3-butadiene;
rac-dimethylsiladiyl(2-ethyl, 4-[3',5'-bis-trifluoromethylphenyl]indenyl)₂zirconium η⁴-1,4-diphenyl-1,3-butadiene;
rac-9-silafluorendiyl(2-n-propyl, 4-[3',5'-bis-trifluoromethylphenyl]indenyl)₂zirconium η⁴-1,4-diphenyl-1,3-butadiene,
rac-9-silafluorendiyl(2-iso-propyl, 4-[3',5'-bis-trifluoromethylphenyl]indenyl)₂zirconium η⁴-1,4-diphenyl-1,3-butadiene;
rac-9-silafluorendiyl(2-n-butyl, 4-[3',5'-bis-trifluoromethylphenyl]indenyl)₂zirconium η⁴-1,4-diphenyl-1,3-butadiene;
rac-9-silafluorendiyl(2-iso-butyl, 4-[3',5'-bis-trifluoromethylphenyl]indenyl)₂zirconium η⁴-1,4-diphenyl-1,3-butadiene;
rac-9-silafluorendiyl(2-sec-butyl, 4-[3',5'-bis-trifluoromethylphenyl]indenyl)₂zirconium η⁴-1,4-diphenyl-1,3-butadiene;
rac-9-silafluorendiyl(2-tert-butyl, 4-[3',5'-bis-trifluoromethylphenyl]indenyl)₂zirconium η⁴-1,4-diphenyl-1,3-butadiene;
rac-9-silafluorendiyl(2-methyl, 4-[3',5'-di-iso-propylphenyl] indenyl)₂zirconium η⁴-1,4-diphenyl-1,3-butadiene;
rac-9-silafluorendiyl(2-ethyl, 4-[3',5'-di-iso-propylphenyl] indenyl)₂zirconium η⁴-1,4-diphenyl-1,3-butadiene;
rac-9-silafluorendiyl(2-n-propyl, 4-[3',5'-di-iso-propylphenyl]indenyl)₂zirconium η⁴-1,4-diphenyl-1,3-butadiene;
rac-9-silafluorendiyl(2-iso-propyl, 4-[3',5'-di-iso-propylphenyl]indenyl)₂zirconium η⁴-1,4-diphenyl-1,3-butadiene;
rac-9-silafluorendiyl(2-n-butyl 4-[3',5'-di-iso-propylphenyl] indenyl)₂zirconium η⁴-1,4-diphenyl-1,3-butadiene;
rac-9-silafluorendiyl(2-iso-butyl, 4-[3',5'-di-iso-propylphenyl]indenyl)₂zirconium η⁴-1,4-diphenyl-1,3-butadiene;
rac-9-silafluorendiyl(2-sec-butyl, 4-[3',5'-di-iso-propylphenyl]indenyl)₂zirconium η⁴-1,4-diphenyl-1,3-butadiene;
rac-9-silafluorendiyl(2-tert-butyl, 4-[3',5'-di-iso-propylphenyl]indenyl)₂zirconium η⁴-1,4-diphenyl-1,3-butadiene;
rac-9-silafluorendiyl(2-methyl, 4-[3',5'-di-iso-propylphenyl] indenyl)₂hafnium η⁴-1,4-diphenyl-1,3-butadiene;
rac-9-silafluorendiyl(2-ethyl, 4-[3',5'-di-iso-propylphenyl] indenyl)₂hafnium η⁴-1,4-diphenyl-1,3-butadiene;
rac-9-silafluorendiyl(2-methyl, 4-[3',5'-di-phenylphenyl] indenyl)₂zirconium η⁴-1,4-diphenyl-1,3-butadiene;
rac-9-silafluorendiyl(2-ethyl, 4-[3',5'-di-phenylphenyl] indenyl)₂zirconium η⁴-1,4-diphenyl-1,3-butadiene;

rac-9-silafluorendiyl(2-n-propyl, 4-[3',5'-di-phenylphenyl] indenyl)$_2$zirconium η$^4$-1,4-diphenyl-1,3-butadiene;
rac-9-silafluorendiyl(2-iso-propyl, 4-[3',5'-di-phenylphenyl] indenyl)$_2$zirconium η$^4$-1,4-diphenyl-1,3-butadiene;
rac-9-silafluorendiyl(2-n-butyl, 4-[3',5'-di-phenylphenyl] indenyl)$_2$zirconium η$^4$-1,4-diphenyl-1,3-butadiene;
rac-9-silafluorendiyl(2-iso-butyl, 4-[3',5'-di-phenylphenyl] indenyl)$_2$zirconium η$^4$-1,4-diphenyl-1,3-butadiene;
rac-9-silafluorendiyl(2-tert-butyl, 4-[3',5'-di-phenylphenyl] indenyl)$_2$zirconium η$^4$-1,4-diphenyl-1,3-butadiene; and
rac-9-silafluorendiyl(2-sec-butyl, 4-[3',5'-di-phenylphenyl] indenyl)$_2$zirconium η$^4$-1,4-diphenyl-1,3-butadiene.

"9-silafluorendiyl-" refers to the substituent:

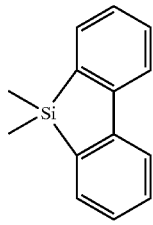

The metallocenes of this invention are prepared according to general techniques known from the literature, for example U.S. Pat. Nos. 5,789,634 and 5,840,644 (both entirely incorporated herein by reference).

Generally, metallocenes of this type are synthesized as shown below where (R$^4$=H) (a) is an aryl-coupling reaction between a 4-halosubstituted indene and an aryl Grignard catalyzed by NiCl2(PPh3)2 in ether-type solvents at room temperature to reflux. Product is usually purified by column chromatography or distillation. (b) is a deprotonation via a metal salt of an alkyl anion (e.g. n-BuLi) to form an indenide followed by reaction with an appropriate bridging precursor as specified in the examples. Reactions are usually done in ether-type solvents at ambient temperatures. The final product is purified by column chromatography of distillation. (c) is double deprotonation via an alkyl anion (e.g. n-BuLi) to form a dianion followed by reaction with a metal halide (e.g. ZrCl$_4$). The reaction are usually done in ether-type or aromatic solvents at ambient temperatures. The final products are obtained by recrystallization of the crude solids.

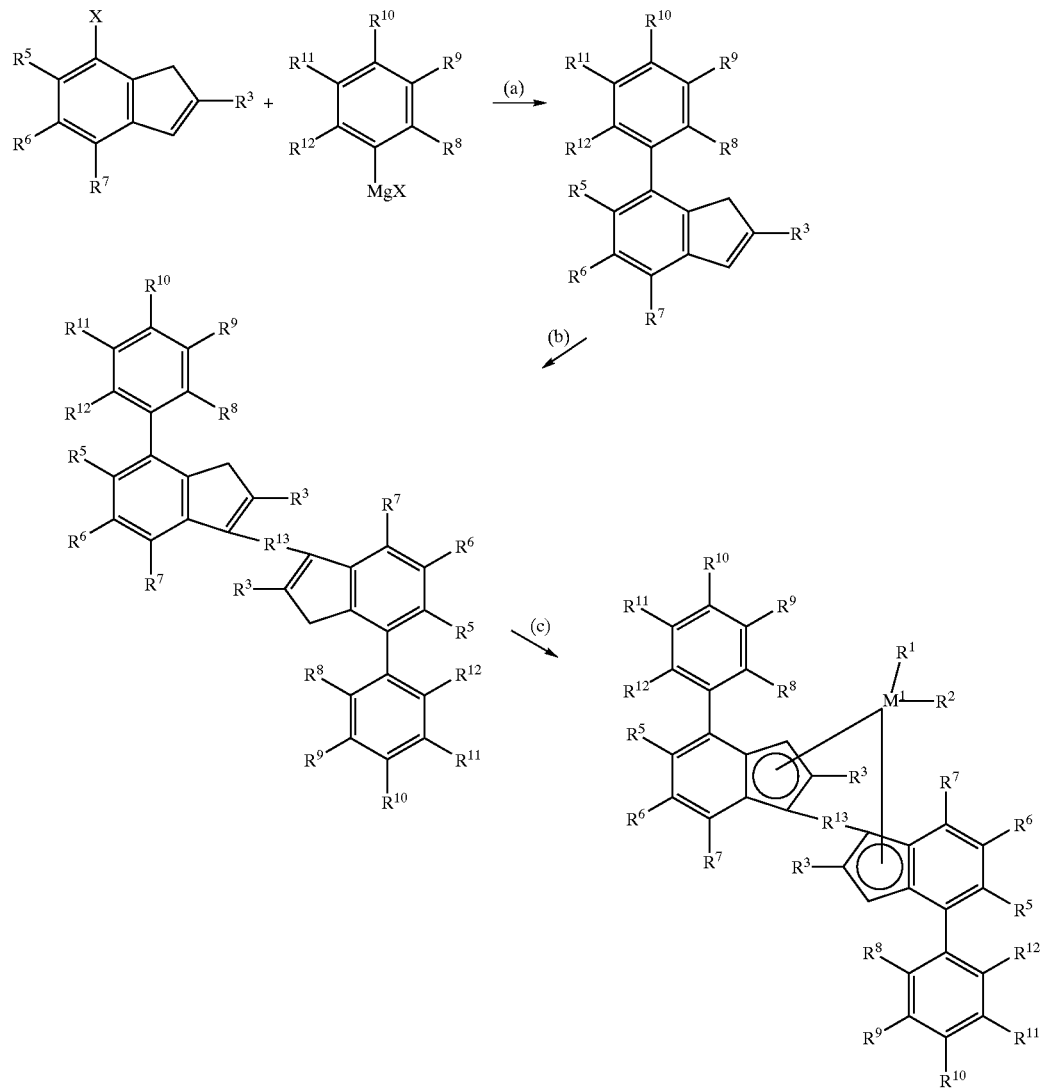

The metallocenes of this invention are highly active catalyst components for the polymerization of olefins. The metallocenes are preferably employed as chiral racemates. However, it is also possible to use the pure enantiomers in the (+) or (−) form. The pure enantiomers allow an optically active polymer to be prepared. However, the meso form of the metallocenes should be removed, since the polymerization-active center (the metal atom) in these compounds is no longer chiral due to the mirror symmetry at the central metal atom and it is therefore not possible to produce a highly isotactic polymer. If the meso form is not removed, atactic polymer is formed in addition to isotactic polymer. For certain applications this may be entirely desirable.

Rac/meso metallocene isomer separation is facilitated when metallocenes containing certain bridging groups are prepared. We have found this to be true when the bridging group, $R^{13}$, is represented by the formula:

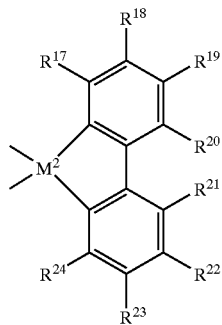

wherein: $M^2$ and $R^{17}$ to $R^{24}$ are as defined above.

Metallocenes are generally used in combination with some form of activator in order to create an active catalyst system. The terms "activator" and "cocatalyst" are used interchangeably and are defined herein to mean any compound or component, or combination of compounds or components, capable of enhancing the ability of one or more metallocenes to polymerize olefins. Alklyalumoxanes such as methylalumoxane (MAO) are commonly used as metallocene activators. Generally alkylalumoxanes contain 5 to 40 of the repeating units:

$R(AlRO)_x AlR_2$ for linear species and $(AlRO)_x$ for cyclic species where R is a $C_1$–$C_8$ alkyl including mixed alkyls. Compounds in which R is methyl are particularly preferred. Alumoxane solutions, particularly methylalumoxane solutions, may be obtained from commercial vendors as solutions having various concentrations. There are a variety of methods for preparing alumoxane, non-limiting examples of which are described in U.S. Pat. Nos. 4,665,208, 4,952, 540, 5,091,352, 5,206,199, 5,204,419, 4,874,734, 4,924,018, 4,908,463, 4,968,827, 5,308,815, 5,329,032, 5,248,801, 5,235,081, 5,103,031 and EP-A-0 561 476, EP-B1-0 279 586, EP-A-0 594-218 and WO 94/10180, each fully incorporated herein by reference.

Ionizing activators may also be used to activate metallocenes. These activators are neutral or ionic, or are compounds such as tri(n-butyl)ammonium tetrakis (pentaflurophenyl)borate, which ionize the neutral metallocene compound. Such ionizing compounds may contain an active proton, or some other cation associated with, but not coordinated or only loosely coordinated to, the remaining ion of the ionizing compound. Combinations of activators may also be used, for example, alumoxane and ionizing activator combination, see for example, WO 94/07928.

Descriptions of ionic catalysts for coordination polymerization comprised of metallocene cations activated by non-coordinating anions appear in the early work in EP-A-0 277 003, EP-A-0 277 004 and U.S. Pat. No. 5,198,401 and WO-A-92/00333 (each incorporated herein by reference). These teach desirable methods of preparation wherein: metallocenes are protonated by an anion precursor such that an alkyl/hydride group is abstracted from a transition metal to make it both cationic and charge-balanced by the non-coordinating anion. Suitable ionic salts include tetrakis-substituted borate or aluminum salts having fluorided aryl-constituents such as phenyl, biphenyl and napthyl.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Non-coordinating anions useful in accordance with this invention are those which are compatible, stabilize the metallocene cation in the sense of balancing its ionic charge at +1, yet retain sufficient lability to permit displacement by an ethylenically or acetylenically unsaturated monomer during polymerization.

The use of ionizing ionic compounds not containing an active proton but capable of producing both the active metallocene cation and a non-coordinating anion is also known. See, for example, EP-A-0 426 637 and EP-A-0 573 403 (each incorporated herein by reference). An additional method of making the ionic catalysts uses ionizing anion precursors which are initially neutral Lewis acids but form the cation and anion upon ionizing reaction with the metallocene compounds, for example the use of tris (pentafluorophenyl) borane. See EP-A-0 520 732 (incorporated herein by reference). Ionic catalysts for addition polymerization can also be prepared by oxidation of the metal centers of transition metal compounds by anion precursors containing metallic oxidizing groups along with the anion groups, see EP-A-0 495 375 (incorporated herein by reference).

Where the metal ligands include halogen moieties (for example, bis-cyclopentadienyl zirconium dichloride) which are not capable of ionizing abstraction under standard conditions, they can be converted via known alkylation reactions with organometallic compounds such as lithium or aluminum hydrides or alkyls, alkylalumoxanes, Grignard reagents, etc. See EP-A-0 500 944 and EP-A1-0 570 982 (each incorporated herein by reference) for in situ processes describing the reaction of alkyl aluminum compounds with dihalo-substituted metallocene compounds prior to or with the addition of activating anionic compounds.

Methods for supporting ionic catalysts comprising metallocene cations and NCA are described in WO 9950311, U.S. Pat. Nos. 5,643,847 and 5,972,823, U.S. patent application Ser. No. 09/184,358, filed Nov. 2, 1998 and U.S. patent application Ser. No. 09/184,389, filed Nov. 2, 1998 (each fully incorporated herein by reference).

When the activator for the metallocene supported catalyst composition is a NCA, preferably the NCA is first added to the support composition followed by the addition of the metallocene catalyst. When the activator is MAO, preferably the MAO and metallocene catalyst are dissolved together in solution. The support is then contacted with the MAO/metallocene catalyst solution. Other methods and order of addition will be apparent to those skilled in the art.

The catalyst systems used to prepare the compositions of this invention are preferably supported using a porous particulate material, such as for example, talc, inorganic oxides, inorganic chlorides such as magnesium chloride, and resinous materials such as polyolefin or polymeric compounds.

Preferably, the support materials are porous inorganic oxide materials, which include those from the Periodic Table of Elements of Groups 2, 3, 4, 5, 13 or 14 metal/metalloid oxides. Silica, alumina, silica-alumina, and mixtures thereof are particularly preferable. Other inorganic oxides that may be employed either alone or in combination with the silica, alumina or silica-alumina are magnesia, titania, zirconia, and the like.

Preferably the support material is porous silica which has a surface area in the range of from 10 to 700 $m^2/g$, a total pore volume in the range of from 0.1 to 4.0 cc/g and an average particle size in the range of from 10 to 500 $\mu$m. More preferably, the surface area is in the range of from 50 to 500 $m^2/g$, the pore volume is in the range of from 0.5 to 3.5 cc/g and the average particle size is in the range of from 20 to 200 $\mu$m. Most desirably the surface area is in the range of from 100 to 400 $m^2/g$, the pore volume is in the range of from 0.8 to 3.0 cc/g and the average particle size is in the range of from 30 to 100 $\mu$m. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

The metallocene, activator and support material may be combined in any number of ways. More than one metallocene may also be used. Examples of suitable support techniques are described in U.S. Pat. Nos. 4,808,561 and 4,701,432 (each fully incorporated herein by reference.). Preferably the metallocenes and activator are combined and their reaction product supported on the porous support material as described in U.S. Pat. No. 5,240,894 and WO 94/28034, WO 96/00243, and WO 96/00245 (each fully incorporated herein by reference.) Alternatively, the metallocenes may be preactivated separately and then combined with the support material either separately or together. If the metallocenes are separately supported, then preferably, they are dried then combined as a powder before use in polymerization.

Regardless of whether the metallocene(s) and their activator are separately precontacted or whether the metallocene (s) and activator are combined at once, in some instances it may be preferred that the total volume of reaction solution applied to porous support is less than 4 times the total pore volume of the porous support, more preferably less than 3 times the total pore volume of the porous support and even more preferably in the range of from more than I to less than 2.5 times the total pore volume of the porous support. Procedures for measuring the total pore volume of porous support are well known in the art. One such method is described in Volume 1, Experimental Methods in Catalyst Research, Academic Press, 1968, pages 67–96.

The supported catalyst system may be used directly in polymerization or the catalyst system may be prepolymerized using methods well known in the art. For details regarding prepolymerization, see U.S. Pat. Nos. 4,923,833 and 4,921,825, and EP 0 279 863 and EP 0 354 893 (each fully incorporated herein by reference).

The metallocene catalyst systems described herein are useful in the polymerization of all types of olefins. This includes polymerization processes which produce homopolymers, copolymers, terpolymers and the like as well as block copolymers and impact copolymers. These polymerization processes may be carried out in solution, in suspension or in the gas phase, continuously or batchwise, or any combination thereof, in one or more steps, preferably at a temperature of from 60° C. to 200° C., more preferably from 30° C. to 80° C., particularly preferably from 50° C. to 80° C. The polymerization or copolymerization is carried out using olefins of the formula $R^aCH=CH-R^b$. In this formula, $R^a$ and $R^b$ are identical or different and are a hydrogen atom or an alkyl radical having 1 to 14 carbon atoms. However, $R^a$ and $R^b$ may alternatively form a ring together with the carbon atoms connecting them. Examples of such olefins are ethylene, propylene, 1-butene, 1-hexene, 4-methyl-1-pentene, 1-octene, norbornene and norbomadiene. In particular, propylene and ethylene are polymerized. The metallocenes and metallocenes catalyst systems of this invention are most suitable for the polymerization of propylene based polymers.

If necessary, hydrogen is added as a molecular-weight regulator and/or in order to increase the activity. The overall pressure polymerization system is from 0.5 to 100 bar. Polymerization is preferably carried out in the industrially particularly interesting pressure range from 5 to 64 bar.

Typically, the metallocene is used in the polymerization in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. When alumoxane is used as the cocatalyst, it is used in a concentration of from $10^{-5}$ to $10^{-1}$ mol, preferably from $10^{-4}$ to $10^{-2}$ mol, per $dm^3$ of solvent or per $dm^3$ of reactor volume. The other cocatalysts mentioned are used in an approximately equimolar amount with respect to the metallocene. In principle, however, higher concentrations are also possible.

If the polymerization is carried out as a suspension or solution polymerization, an inert solvent which is customary for the Ziegler low-pressure process is typically used for example, the polymerization is carried out in an aliphatic or cycloaliphatic hydrocarbon; examples of which are propane, butane, hexane, heptane, isooctane, cyclohexane and methylcyclohexane. It is also possible to use a benzene or hydrogenated diesel oil fraction. Toluene can also be used. The polymerization is preferably carried out in the liquid monomer. If inert solvents are used, the monomers are metered in gas or liquid form.

Before addition of the catalyst, in particular of the supported catalyst system, another alkylaluminum compound, such as, for example, trimethylaluminum, triethylaluminum, triisobutylaluminum, trioctylaluminum or isoprenylaluminum, may additionally be introduced into the reactor in order to render the polymerization system inert (for example to remove catalyst poisons present in the olefin). This compound is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This allows the molar $Al/M^1$ ratio to be selected at a low level in the synthesis of a supported catalyst system.

In principle, however, the use of further substances for catalysis of the polymerization reaction is unnecessary, i.e.

the systems according to the invention can be used as the only catalysts for the polymerization of olefins.

The process according to the invention is distinguished by the fact that the metallocenes described can give propylene polymers of very high molecular weight, melting point, and very high stereotacticity, with high catalyst activities in the industrially particularly interesting polymerization temperature range of from 50° C. to 80° C.

The catalyst systems of this invention are capable of providing polymers, particularly propylene homopolymers and copolymers, of exceptionally high molecular weight and melting point even when used in processes under commercially relevant conditions of temperature, pressure and catalyst activity. Preferred melting points are at least as high as 155° C., more preferably at least 157° C., even more preferably at least 157° C., and most preferably 160° C. or more.

The catalyst systems of this invention are also capable of providing propylene polymers having high stereospecificity and regiospecificity. Isotactic propylene polymers prepared according to the processes of this invention may have a proportion of 2-1-inserted propene units of less than 0.5%, at a triad tacticity of greater than 98%. Preferably there is no measurable proportion of 2-1-inserted propene units. Triad tacticity is determined using $^{13}$C-NMR according to J. C. Randall, Polymer Sequence Determination: Carbon-13 NMR Method, Academic Press New York 1978. Polymers prepared using the processes of described herein find uses in all applications including fibers, injection-molded parts, films, pipes etc.

While the present invention has been described and illustrated by reference to particular embodiments, it will be appreciated by those of ordinary skill in the art, that the invention lends itself to many different variations not illustrated herein. For these reasons, then, reference should be made solely to the appended claims for purposes of determining the true scope of the present invention.

Although the appendant claims have single appendencies in accordance with U.S. patent practice, each of the features in any of the appendant claims can be combined with each of the features of other appendant claims or the main claim.

EXAMPLES

All air sensitive experiments are carried out in nitrogen purged dry boxes. All solvents were purchased from commercial sources. 4-Bromo-2-methyl indene, 4-chloro-2-methyl-indene and tris (perfluorophenyl) borane in toluene were purchased from commercial sources. Aluminum alkyls were purchased as hydrocarbon solutions from commercial sources. The commercial methylalumoxane ("MAO") was purchased from Albemarle as a 30 wt % solution in toluene. The metallocenes racemic dimethylsiladiyl(2-methyl-4-phenylindenyl)$_2$ zirconium dichloride and racemic dimethylsiladiyl(4-[1-naphthy]-2-methylindenyl)$_2$ zirconium dichloride were obtained from commercial sources.

Comparative Example 1 racemic dimethylsiladiyl(2-methyl-4phenylindenyl)$_2$ zirconium dichloride

Supported Comparison Metallocene Catalyst System 1 racemic dimethylsiladiyl(2-methyl-4-phenylindenyl)$_2$zirconium dichloride/MAO

In a 100 mL round bottom flask racemic dimethylsiladiyl (2-methyl-4-phenylindenyl)$_2$ zirconium dichloride (Comparison metallocene 1, 0.055 g) was added to a MAO solution (6.74 g, 7.2 mL) and stirred twenty minutes. This was filtered through a medium glass frit funnel and washed with toluene (14 mL). To the combined filtrates was added dehydrated silica (4.0 g, Davison 948 Regular, 600° C. dehydration). This slurry was stirred for twenty minutes then dried at 40° C. for two minutes under vacuum on a rotary evaporator until the liquid evaporated, and then the solid was further dried a total of about two hours and twenty two minutes. The supported catalyst was recovered as a light orange, free flowing solid (5.63 g).

Comparative Example 2 racemic dimethylsiladiyl(2-methyl-4-[1-naphthy] indenyl)$_2$zirconium dichloride Supported Comparison Metallocene Catalyst System 2 racemic dimethylsiladiyl(2-methyl-4-[1-naphthy] indenyl)$_2$zirconium dichloride/MAO In a 100 mL round bottom flask racemic dimethylsiladiyl (2-methyl-4-[1-naphthy]indenyl)$_2$ zirconium dichloride (Comparison metallocene 2, 0.064 g) was added to a MAO solution (6.74 g, 7.2 mL) and stirred twenty minutes. This was filtered through a medium glass frit funnel and washed with toluene (14 mL). To the combined filtrates was added dehydrated silica (4.0 g, Davison 948 Regular, 600° C. dehydration). This slurry was stirred for twenty minutes then dried at 40° C. for two minutes under vacuum on a rotary evaporator until the liquid evaporated, and then the solid was further dried a total of about two hours. The supported catalyst was recovered as an orange, free flowing solid (4.72 g).

Example 3 racemic [9-silafluorenebis(4-(3',5'-di-t-butylphenyl)-2-methylindene]zirconium dichloride 4-[3',5'-di-t-butylphenyl]-2-methylindene 4-Chloro-2-methylindene (6.1 g, 37 mmol) and NiCl$_2$(Ph$_3$)$_2$ (1.8 g, 2.8 mmol) were dissolved in 150 mL of Et$_2$O. 3,5-Di-t-butylphenylnagnesium bromide (10 g, 37 mmol) as a Et$_2$O solution was added to the solution and the reaction was stirred overnight at room temperature. After overnight stirring, the reaction was slowly quenched with H$_2$O to neutralize unreacted Grignard. The solution was subsequently treated with 100 mL of 10% HCl(aq), neutralized with saturated sodium bicarbonate aqueous solution. The organic layer was dried with magnesium sulfate and the solvent was removed by rotary evaporation. The remaining residue was loaded onto a silica gel column and eluted with hexane. Yield was 4.6 g (40%).

lithium 4-[3',5'-di-t-butylphenyl]-2-methylindene

4-[3',5'-Di-t-butylphenyl]-2-methylindene (4.7 g, 15 mmol) was dissolved in 80 mL of pentane. To this solution was added 5.9 mL of n-BuLi (2.5M in hexane) and the reaction is allowed to stir 4 hours at room temperature. A white solid precipitated from solution and was collected by frit filtration and washed with additional pentane. Yield was 3.6 g (78%).

9-silafluorenebis[4-(3',5'-di-t-butylphenyl)-2-methylindene 9,9-Dichloro-9-silafluorene (1.2 g, 9.2 mmol) was dissolved in 80 mL of THF. To this solution was slowly added lithium 4-(3',5'-di-t-butylphenyl)-2-methylindene (3.0 g, 9.2 mmol) as a dry powder and the solution was stirred overnight. After this time, the solvent was removed in vacuo and the residue was taken up in diethyl ether. The solution was filtered through a frit to remove LiCl and the solvent was removed in vacuo and used as a crude product (4.1 g) for the next step.

[9-silafluorenebis(4-(3',5'-di-t-butylphenyl)-2-methylindene]ZrCl$_2$

The crude solid from the previous step (4.1 g, 5.5 mmol) was taken up in 50 mL of diethyl ether. To this solution was slowly added n-BuLi (4.4 mL, 2.5 M in hexane) and stirred for 3 hours at room temperature. The solution was cooled to −30° C. and ZrCl$_4$ (1.28 g, 4.6 mmol) was added as a dry powder and stirred at room temperature for 2 hours. The solvent was removed in vacuo and toluene was added to the crude residue. The solution was filtered to remove LiCl. The filtrate was concentrated and pentane is added under heating. The solution was cooled to induce crystallization. Yield of pure racemic isomer was 187 mg (3.7%).

Supported Metallocene Catalyst System 3 racemic [9-silafluorenebis(4(3',5'-di-t-butylphenyl)-2-methylindene]zirconium dichloride In a 100 mL round bottom flask racemic [9-Silafluorenebis(4-(3',5'-di-t-butylphenyl)-2-methylindene]zirconium dichloride (0.085 g) was added to a MAO solution (6.74 g, 7.2 mL) and stirred twenty minutes. This was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated, and then the solid was further dried a total of about two hours and twenty minutes. The supported catalyst was recovered as a pink reddish, free flowing solid (5.24 g).

Example 4 racemic [9-silafluorenebis(4-(3',5'-di-t-butylphenyl)-2-isopropylindene]zirconium dichloride 4-[3',5'-di-t-butylphenyl]-2-isopropylindene 4-Chloro-2-isopropylindene (7.2 g, 37 mmol) and NiCl$_2$PPh$_3$)$_2$ (1.8 g, 2.8 mmol) were dissolved in 150 mL of Et$_2$O. 3,5-Di-di-t-butylphenylmagnesium bromide (10 g, 37 mmol) as a Et$_2$O solution was added to the solution and the reaction was stirred overnight at room temperature. After overnight stirring, the reaction was slowly quenched with H$_2$O to neutralize unreacted Grignard. The solution was subsequently treated with 100 mL of 10% HCl(aq), neutralized with saturated sodium bicarbonate aqueous solution. The organic layer was dried with magnesium sulfate and the solvent was removed by rotary evaporation. The remaining residue was loaded onto a silica gel column and eluted with hexane. Yield is 5.8 g (45%).

lithium 4-[3',5'-di-t-butylphenyl]-2-isopropylindene

4-[3',5'-di-t-butylphenyl]-2-isopropylindene (5.8 g, 17 mmol) was dissolved in 80 mL of pentane. To this solution was added 6.6 mL of n-BuLi (2.5M in hexane) and the reaction was allowed to stir 4 hours at room temperature. A white solid precipitated from solution and was collected by frit funnel filtration and washed with additional pentane. Yield is 5.0 g (87%).

silafluorenebis[4-(3',5'-bis[t-butyl]phenyl)-2-isopropylindene 9,9-Dichloro-9-silafluorene (1.1 g, 8.5 mmol) was dissolved in 80 mL of THF. To this solution was slowly added lithium 4-(3',5'-di-t-butylphenyl)-2-isopropylindene (3.0 g, 8.5 mmol) as a dry powder and the solution was stirred overnight. After this time, the solvent was removed in vacuo and the residue was taken up in diethyl ether. The solution as filtered through frit to remove LiCl and the solvent was removed in vacuo and used as a crude product (3.9 g) for the next step.

9-silafluorenebis(4-(3',5'-di-t-butylphenyl)-2-isopropylindene]ZrCl$_2$

The crude solid from the previous step (3.9 g, 4.6 mmol) was taken up in 50 mL of diethyl ether. To this solution was slowly added n-BuLi (3.7 mL, 2.5 M in hexane) and stirred for 3 hours at room temperature. The solution was cooled to −30° C. and ZrCl$_4$ (1.1 g, 4.6 mmol) was added as a dry powder and stirred at room temperature for 2 hours. The solvent was removed in vacuo and toluene was added to the crude residue. The solution was filtered to remove LiCl. The filtrate was concentrated and pentane added under heating. The solution was cooled to induce crystallization. Yield of pure racemic isomer was 280 mg (6.0%).

Supported Metallocene Catalyst System 4 racemic [9-silafluorenebis(4(3',5'-di-t-butylphenyl)-2-isopropylindene]zirconium dichloride In a 100 mL round bottom flask racemic [[9-Silafluorenebis(4-(3',5'-di-t-butylphenyl)-2-isopropylindene]zirconium dichloride (0.090 g) was added to a MAO solution (6.74 g, 7.2 mL) and stirred twenty minutes. This was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about two hours and twenty minutes. The supported catalyst was recovered as a light purple, free flowing solid (5.17 g).

Example 5

[9-silafluorenebis(4-(3',5'-dimethylphenyl)-2-isopropylindene]zirconium dichloride 2,2'-Dibromobiphenyl To a stirred solution of o-dibromobenzene (47.3 g, 0.2 mol) in 450 mL of anhydrous THF was added 76.4 mL of n-BuLi (1.0M in Et$_2$O). The o-dibromobenzene solution was cooled in a dry ice/acetone bath. The yellow-green reaction mixture was allowed to warm to 5° C. and was then hydrolyzed with 100 mL of 5% hydrochloric acid. The resulting layers were separated and the aqueous layer extracted 4 times with 4×20 mL portions of diethyl ether. The ether washings were combined with the original organic layer and dried over sodium sulfate, filtered, and concentrated by distillation until the distillation temperature reached 70° C. The residue was treated with 50 mL of absolute ethanol and cooled to give 2,2'-dibromobiphenyl. Yield was 2.32 g (7.4%)

9,9-Dichloro-9-silafluorene

Lithium wire (3.33 g, 0.08 mol) was washed with pentane, carefully cut into small pieces, and suspended in 150 mL of $Et_2O$. While stirring, 2,2-dibromobiphenyl (25 g, 0.08 mol) in 100 mL of diethyl ether was added dropwise over 1 hour and the contents were allowed to stir for 10 hours. The mixture was filtered through a frit to remove any unreacted Li and LiBr. The filtrate was loaded into an addition funnel and slowly dropped into a solution containing $SiCl_4$ (50 g, 0.08 mol) in 200 mL of $Et_2O$. After addition, the contents were stirred at room temperature for 5 hours. The solvent was removed in vacuo and 300 mL of pentane was added. The solution was filtered to remove LiCl and the solvents were again removed in vacuo. The solids were then loaded into a sublimator and allowed to sublime at 150° C. under full vacuum. Yield was 10.0 g (51%).

4-(3',5'-dimethylphenyl)-2-isopropylindene 4-chloro-2-isopropylindene (10 g, 54 mmol) and $NiCl_2(PPh_3)_2$ (1.8 g, 2.8 mmol) were dissolved in 150 mL of $Et_2O$. 3,5-Dimethylphenylmagnesium bromide (54 mmol) as a $Et_2O$ solution was added under vigorous stirring and the reaction was stirred overnight at room temperature. After overnight stirring, the reaction was slowly quenched with $H_2O$ to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield was 5.5 g (39%).

lithium 4-3',5'-dimethylphenyl)2-isopropylindene 4-(3',5'-dimethylphenyl)-2-methylindene (5.6 g, 24 mmol) was dissolved in 80 mL of pentane. To this solution was added 9.6 mL of n-BuLi (2.5M in hexane) and the reaction was allowed to stir 4 hours at room temperature. A white solid precipitated from solution and was collected by frit filtration and washed with additional pentane. Yield was 4.5 g (80%).

9-silafluorenebis(4-(3,5'-dimethylphenyl)-2-isopropylindene 9,9-dichloro-9-silafluorene (1.4 g, 11 mmol) was dissolved in 80 mL of THF. To this solution was slowly added lithium 4-(3',5'-dimethylphenyl)-2-methylindene (3.0 g, 11 mmol) as a dry powder and the solution was stirred overnight. After this time, the solvent was removed in vacuo and the residue was taken up in diethyl ether. The solution was filtered through frit to remove LiCl and the solvent was removed in vacuo and used as a crude product (2.1 g) for the next step.

[9-silafluorenebis(4-(3',5'-dimethylphenyl)-2-isopropylindene]$ZrCl_2$

The crude solid from the previous step (2.1 g, 3.2 mmol) was taken up in 50 mL of diethyl ether. To this solution was slowly added n-BuLi (2.56 mL, 2.5 M in hexane) and then stirred for 3 hours at room temperature. The solution was cooled to −30° C. and $ZrCl_4$ (0.74 g, 3.2 mmol) was added as a dry powder and stirred at room temperature for 2 hours. The solvent was removed in vacuo and toluene was added to the crude residue. The solution was filtered to remove LiCl. The filtrate was concentrated and pentane was added under heating. The solution was cooled to induce crystallization. Yield of pure rac/meso metallocene was 120 mg (3.8%).

Supported Metallocene Catalyst System 5

Rac/meso [9-silafluorenebis(4-(3',5'-dimethylphenyl)-2-isopropylindene]zirconium dichloride/MAO In a 100 mL round bottom flask rac/meso [9-silafluorenebis(4-(3',5'-dimethylphenyl)-2-isopropylindene]zirconium dichloride (0.076 g) was added to the MAO solution (6.74 g, 7.2 mL) and stirred twenty minutes. This was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated, and then the solid was further dried a total of about 2 hours and thirty minutes. The supported catalyst was recovered as a dull purple, free flowing solid (5.06 g).

Example 6 rac-9-silafluorenebis(2-methylindenyl)zirconium dimethyl

9-Silafluorene, 9,9-bis-2-Methylindene

Solid 2-Methylindenyl lithium (3.34 g, 24.52 mmol) was added to a stirred solution of 9,9-Dichloro,9-silafluorene (3.08 g, 12.26 mmol) in $Et_2O$ (ca. 25 mL) and the resultant mixture was stirred at room temperature for 2 hours. The solvent was removed and the residue was extracted into $CH_2Cl_2$ (ca. 75 mL), filtered and the solvent removed giving a white powder which was washed with pentane (ca 50 mL) and dried under vacuum leaving 9-Silafluorene, 9,9-bis-2-Methylindene as a white powder (3.80 g, 71%).

Preparation of 9-Silafluorene, 9,9-bis-2-Methylindenyl dilithium

A slurry of 9-Silafluorene, 9,9-bis-2-Methylindene (3.80 g, 8.66 mmol) in $Et_2O$ (ca. 25 mL) was treated with n-butyllithium (12 mL of a 1.6 M solution in hexanes) and the resultant mixture stirred for 1 hour at room temperature producing a pale yellow precipitate. The mixture was filtered to isolate the pale yellow solid which was dried under vacuum giving 9-Silafluorene, 9,9-bis-2-Methylindenyl dilithium.$(Et_2O)_{0.5}$ (3.80 g, 88%).

Preparation of 9-Silafluorene,9,9-bis-2-Methylindenyl Zirconium Dimethyl

A mixture of 9-Silafluorene, 9,9-bis-2-Methylindenyl dilithium.$(Et_2O)_{0.5}$ (1.83 g, 3.69 mmol) and $ZrCl_4$ (0.95g, 4.08 mmol) in benzene (ca. 25 mL) was stirred for 80 minutes at room temperature producing an orange solid. The mixture was filtered and the orange solid was washed with hexane. Upon mixing with the benzene filtrate, the hexane wash produced a yellow solid and this mixture was filtered to remove the yellow solid. The solvents were removed from the resulting benzene-hexane filtrate producing an orange solid. The second orange solid was washed once with benzene and twice with pentane and dried under vacuum. A slurry of this orange solid in benzene (ca. 10 mL) was treated with $CH_3MgBr$ (0.8 mL of a 3.0 M solution in $Et_2O$) and the mixture was stirred for 15 minutes at room temperature. Dioxane (ca. 2–3 mL) was added to the mixture which was filtered to produce a clear yellow filtrate. The solvents were removed from the filtrate under vacuum giving pure rac-9-Silafluorene,9,9-bis-2-Methylindenyl Zirconium Dimethyl (0.035 g, 1.7%).

Polymerizations

Isotactic Polypropylene Homopolymer

The polymerization procedure for producing homopolymers with the supported catalyst systems prepared as described above (except for Example 6 which is described below) was as follows. In a clean, dry two liter autoclave which had been flushed with propylene vapor, TEAL scavenger (0.3 mL, 1.5M) was added. Hydrogen gas was added at this point if indicated. The quantity of hydrogen is 1.55 millimoles for each psi added as shown in the Tables. The reactor was closed and filled with 800 mL liquid propylene. After heating the reactor to the indicated polymerization temperature, the catalyst was added by washing in with propylene (200 mL). After the indicated time, typically one hour, the reactor was cooled, and the excess propylene vented. The polymer was removed and dried.

Polymerization Using rac-9-silafluorenebis(2-methylindenyl)zirconium dimethyl as Catalyst Precursor—Isotactic Polypropylene Homopolymer Procedure A solution of triisobutylaluminum (TIBAL) scavenger (0.3 mL of a 10% by volume solution in toluene) in toluene (0.7 mL) was added to a dry clean two liter autoclave under a nitrogen purge. The autoclave was filled with 300 mL of liquid propylene and heated to 60° C. The catalyst, formed by reacting the catalyst precursor and the trityltetrakisperfluorophenylborate activator in equimolar amounts in toluene (ca 1–1.5 mL) for a period of five minutes, was flushed into the autoclave with 100 mL of propylene. The polymerizations were carried out for fifteen minutes after which the reactor was cooled and the excess propylene was vented. The polymer was removed and dried.

Random Copolymer (RCP)

The polymerization procedure for producing random copolymers with the supported catalyst systems prepared as described above was as follows. In a clean, dry two liter autoclave which had been flushed with propylene vapor, TEAL scavenger (0.3 mL, 1.5M) was added. Hydrogen gas was added at this point if indicated. The quantity of hydrogen is 1.55 millimoles for each psi added as shown in the Tables. The reactor was closed and filled with 800 mL liquid propylene. After heating the reactor to 60° C., a partial pressure of ethylene was added as indicated and then the catalyst was added by washing in with propylene (200 mL). Ethylene gas was fed to maintain a constant pressure. After the indicated time, typically one hour, the reactor was cooled, and the excess propylene and ethylene vented. The polymer was removed and dried.

Impact Copolymers (ICP)

The polymerization procedure for producing ICP with the supported catalyst systems prepared as described above was as follows. In a clean, dry two liter autoclave which had been flushed with propylene vapor, TEAL scavenger (0.3 mL, 1.5M) was added. Hydrogen gas was added at this point. The quantity of hydrogen is 1.55 millimoles for each psi added as shown in the Tables. The reactor was closed and filled with 800 mL liquid propylene. After heating the reactor to 70° C., the catalyst was added by washing in with propylene (200 mL). After the indicated time, typically one hour, the reactor was vented to about 170 psig pressure and then an ethylene/propylene gas mixture was passed through the reactor at the rates indicated while maintaining 200 psig. At the end of the gas phase stage, typically 90 to 150 minutes, the reactor was vented and cooled under $N_2$. The granular ICP polymer was removed and dried.

Polymerization run numbers 1–14 were made using Supported Comparison Metallocene Catalyst System 1. Results are reported in Tables 1 and 2.

Polymerization run numbers 15–25 made using Supported Comparison Metallocene Catalyst System 2 Results are reported in Tables 3 and 4.

Polymerization run numbers 65–71 were made using Supported Metallocene Catalyst System 3. Results are reported in Tables 5 and 6.

Polymerization run numbers 72–88 were made using Supported Metallocene Catalyst System 4. Results are reported in Tables 7 and 8.

Polymerization run numbers 133 and 134 were made using Supported Metallocene Catalyst System 5. Results are reported in Tables 9 and 10.

Polymerization run numbers 135 and 136 were made using Metallocene Catalyst System 6. Results are reported in Table 11.

Polymer Analysis

Molecular weight determinations were made by gel permeation chromatography (GPC) according to the following technique. Molecular weights and molecular weight distributions were measured using a Waters 150C gel permeation chromatography equipped with Shodex (Showa Denko) AT-806MS columns and a differential refractive index (DRI) detector operating at 145° C. with 1,2,4-trichlorobenzene as the mobile phase at a 1.0 mL/min. flow rate. The sample injection volume was 300 microliters. The columns were calibrated using narrow polystyrene standards to generate a universal calibration curve. The polypropylene calibration curve was established using $k=8.33 \times 10^{-5}$ and $a=0.800$ as the Mark-Houwink coefficients. The numerical analyses were performed using Waters "Expert-Ease" software running on a VAX 6410 computer.

Ethylene amounts in the random copolymers were determined by FT-IR using a calibration obtained from samples whose composition was determined by NMR.

DSC melting points were determined on commercial DSC instruments and are reported as the second melting point. The polymer granules weighing less than 10 milligrams were heated to 230.0° C. for ten minutes and then cooled from 230° C. to 50° C. at 10° C./minute. The sample is held at 50° C. for five minutes. The second melt is then recorded as the sample is heated from 50° C. to 200° C. at a rate of 10° C./minute. The peak temperature is recorded as the second melting point.

ICP Polymer Extraction Method

The ICP polymer was dissolved in hot xylene and then allowed to cool overnight. After filtration the insolubes are dried. The xylene soluble portion was evaporated and the soluble material recovered. The IV of the recovered soluble material was measured in decalin at 135° C. by using know methods and instruments such as a Schott A VSPro Viscosity Automatic Sampler.

At very high ICP MFR this method can extract some low molecular weight isotactic PP and thus lower the observed IV.

ICP Polymer Fractionation Method

The ICP samples were sent to Polyhedron Laboratories, Inc. to be fractionated and analyzed by GPC. A generally described of the procedure is found in the reference J. C. Randall, J. Poly. Sci.: Part A Polymer Chemistry, Vol. 36, 1527–1542(1998).

TABLE 1 racemic dimethylsiladiyl(2-methyl-4-phenylindenyl)$_2$ zirconium dichloride/MAO - comparison

| RUN # | Metallocene Catalyst System (Comparison) | TEMP. (° C.) | Cat Amount (mg) | Yield (g) | Efficiency (Kg/g cat) | C$_2$= (delta psi) | H2 (delta psi) | Time split (min.) | C$_2$=/C$_3$= flow rates (l/min.) |
|---|---|---|---|---|---|---|---|---|---|
| 1  | 1 | 60 | 67 | 274.7 | 4.10 | 0  | 0  | 60 | — |
| 2  | 1 | 60 | 45 | 71.7  | 1.59 | 0  | 0  | 60 | — |
| 3  | 1 | 60 | 40 | 134.1 | 3.35 | 10 | 0  | 60 | — |
| 4  | 1 | 60 | 42 | 221.5 | 5.27 | 20 | 0  | 60 | — |
| 5  | 1 | 60 | 30 | 121.3 | 4.04 | 55 | 0  | 60 | — |
| 6  | 1 | 60 | 30 | 130.2 | 4.34 | 70 | 0  | 60 | — |
| 7  | 1 | 60 | 30 | 101.8 | 3.39 | 20 | 0  | 60 | — |
| 8  | 1 | 70 | 45 | 293.5 | 6.52 | —  | 50 | 60 | — |
| 9  | 1 | 70 | 31 | 198.9 | 6.42 | —  | 50 | 60 | — |
| 10 | 1 | 70 | 30 | 291.9 | 9.73 | —  | 50 | 60/150 | 4.0/1.0 |
| 11 | 1 | 70 | 30 | 231.3 | 7.71 | —  | 50 | 60/90  | 4.0/1.0 |
| 12 | 1 | 70 | 30 | 224.8 | 7.49 | —  | 50 | 60/90  | 4.1/0.9 |
| 13 | 1 | 70 | 30 | 209.9 | 7.00 | —  | 50 | 60/90  | 3.6/1.4 |
| 14 | 1 | 70 | 30 | 208.2 | 6.94 | —  | 50 | 60/90  | 4.0/1.0 |

TABLE 2 racemic dimethylsiladiyl(2-methyl-4-phenylindenyl)$_2$ zirconium dichloride/MAO - comparison

| RUN # | Metallocene Catalyst System (Comparison) | Total Ethylene (wt %) | Ethylene in Rubber (wt %) | Total Rubber (wt %) | Final MFR (g/10 min.) | Melting Point (° C.) | MW | MWD | IV Of Copolymer |
|---|---|---|---|---|---|---|---|---|---|
| 1  | 1 | —     | —     | —     | 0.16   | 149.2  | 600.0 | 2.00 | — |
| 2  | 1 | —     | —     | —     | 0.54   | 148.2  | 664.9 | 1.92 | — |
| 3  | 1 | 0.67  | —     | —     | 0.84   | 142.0  | 349.0 | 2.09 | — |
| 4  | 1 | 1.28  | —     | —     | 2.57   | 138.4  | 280.0 | 1.95 | — |
| 5  | 1 | 3.77  | —     | —     | 6.48   | 121.4  | 255.0 | 2.04 | — |
| 6  | 1 | 4.43  | —     | —     | 5.95   | 116.0  | 301.0 | 2.30 | — |
| 7  | 1 | 1.44  | —     | —     | 2.05   | 137.5  | 330.4 | 2.23 | — |
| 8  | 1 | —     | —     | —     | 99.6   | 150.3  | 120.6 | 3.01 | — |
| 9  | 1 | —     | —     | —     | 58.95  | 150.9  | 135.7 | 3.15 | — |
| 10 | 1 | 13.23 | 49.20 | 26.89 | 178.5  | 151.2  | 81.2  | 3.37 | 0.7520 |
| 11 | 1 | 7.58  | 47.37 | 16.00 | 134.05 | 150.6  | 98.4  | 3.25 | 0.687 |
| 12 | 1 | 7.82  | 50.04 | 15.63 | 127.16 | 150.0  | 100.4 | 3.11 | 0.708 |
| 13 | 1 | 5.3   | 38.96 | 13.60 | 201.9  | 150.43 | 91.2  | 3.28 | 0.779 |
| 14 | 1 | 0.47  | 64.32 | 0.73  | 97.1   | 150.8  | 116.8 | 3.42 | not submit. |

TABLE 3 racemic dimethylsiladiyl(2-methyl-4-[1-naphthy]indenyl)$_2$ zirconium dichloride/MAO - comparison

| RUN # | Metallocene Catalyst System (comparison) | Cat Amount (mg) | Yield (g) | Efficiency (Kg/g cat) | C$_2$= (delta psi) | H2 (delta psi) | Time split (min.) | C$_2$=/C$_3$= flow rates (l/min.) |
|---|---|---|---|---|---|---|---|---|
| 15 | 2 | 76 | 332.0 | 4.37 | —  | 40 | 60 | — |
| 16 | 2 | 61 | 260.8 | 4.28 | —  | 35 | 60/120 | 4.0/1.0 |
| 17 | 2 | 60 | 266.2 | 4.44 | —  | 35 | 60/120 | 4.4/0.6 |
| 18 | 2 | 60 | 272.6 | 4.54 | —  | 35 | 60/120 | 4.2/0.8 |
| 19 | 2 | 61 | 196.9 | 3.23 | —  | 35 | 60 | — |
| 20 | 2 | 61 | 121.2 | 1.99 | 20 | 5  | 60 | — |
| 21 | 2 | 61 | 118.1 | 1.94 | 30 | 5  | 60 | — |
| 22 | 2 | 61 | 137.7 | 2.26 | 40 | 5  | 60 | — |
| 23 | 2 | 62 | 141.9 | 2.29 | 50 | 5  | 60 | — |
| 24 | 2 | 60 | 138.6 | 2.31 | 40 | 10 | 60 | — |
| 25 | 2 | 62 | 234.8 | 3.79 | —  | 50 | 60/90 | 4.0/1.0 |

TABLE 4 racemic dimethylsiladiyl(2-methyl-4-[1-naphthyl]indenyl)₂ zirconium dichloride/MAO - comparison

| RUN # | Metallocene Catalyst System (comparison) | Total Ethylene (wt %) | Ethylene in Rubber (wt %) | Total Rubber (wt %) | Final MFR (g/10 min.) | Melting Point (° C.) | MW | MWD | IV of Copolymer |
|---|---|---|---|---|---|---|---|---|---|
| 15 | 2 | — | — | — | 4.08 | 150.5 | 299.1 | 2.78 | — |
| 16 | 2 | 7.76 | 47.27 | 16.42 | 4.76 | 151.7 | 212.1 | 2.68 | 1.6567 |
| 17 | 2 | 16.39 | 61.45 | 26.67 | 1.3 | 150.8 | 230.9 | 3.33 | 1.7048 |
| 18 | 2 | 9.74 | 51.52 | 18.91 | 4.98 | 151.0 | 210.4 | 2.96 | 1.7127 |
| 19 | 2 | — | — | — | 3.12 | 151.0 | 278.0 | 2.49 | — |
| 20 | 2 | 1.27 | — | — | 0.19 | 138.43 | 603.0 | 2.59 | — |
| 21 | 2 | 1.75 | — | — | 0.15 | 136.10 | 614.8 | 2.59 | — |
| 22 | 2 | 2.25 | — | — | 0.196 | 131.90 | 604.5 | 2.31 | — |
| 23 | 2 | 2.82 | — | — | 0.213 | 127.83 | 579.0 | 2.36 | — |
| 24 | 2 | 2.39 | — | — | 0.225 | 131.63 | 542.8 | 2.41 | — |
| 25 | 2 | 3.803 | 48.39 | 7.86 | 4.95 | 151.43 | 176.8 | 2.94 | 1.425 |

TABLE 5 racemic[9-silafluorenebis(4-(3',5'-di-t-butylphenyl)-2-methylindenYL]zirconium dichloride/MAO

| RUN # | Metallocene Catalyst System | Cat Amount (mg) | TEMP. (° C.) | Yield (g) | Efficiency (Kg/g cat) | H2 (delta psi) | Time split (min.) | $C_2=/C_3=$ flow rates (l/min.) |
|---|---|---|---|---|---|---|---|---|
| 65 | 3 | 299 | 60 | 13.2 | 0.04 | 0 | 6 | — |
| 66 | 3 | 61 | 60 | 35.0 | 0.57 | 0 | 60 | — |
| 67 | 3 | 60 | 70 | 81.3 | 1.4 | 35 | 60 | — |
| 68 | 3 | 32 | 70 | 96.2 | 3.0 | 35 | 60/90 | 4.0/1.0 |
| 69 | 3 | 30 | 70 | 93.3 | 3.1 | 35 | 60/120 | 4.0/1.0 |
| 70 | 3 | 31 | 70 | 83.9 | 2.7 | 35 | 60/90 | 3.6/1.4 |
| 71 | 3 | 30 | 70 | 77.8 | 2.6 | 35 | 60/120 | 4.2/0.8 |

TABLE 6 racemic[9-silafluorenebis(4-(3',5'-di-t-butylphenyl)-2-methylindenyl]zirconium dichloride/MAO

| RUN # | Metallocene Catalyst System | Total Ethylene (wt %) | Ethylene in Rubber (wt %) | Total rubber (wt %) | Final MFR (g/10 min.) | Melting Point (° C.) | MW | MWD | IV of Copolymer |
|---|---|---|---|---|---|---|---|---|---|
| 65 | 3 | — | — | — | 0.65 | 156.17 | 412 | 149.3 | — |
| 66 | 3 | — | — | — | 0.075 | 156.23 | 710.8 | 2.71 | — |
| 67 | 3 | — | — | — | 3.59 | 156.5 | 270.7 | 2.82 | — |
| 68 | 3 | 4.814 | 54.74 | 8.8 | 69.59 | 155.43 | 119.4 | 3.22 | |
| 69 | 3 | 6.624 | 49.55 | 13.4 | 9.84 | 156.5 | 200.0 | 3.56 | |
| 70 | 3 | 3.095 | 42.72 | 7.2 | 14.54 | 155.97 | 194.5 | 3.52 | |
| 71 | 3 | 7.691 | 54.36 | 14.1 | 10.61 | 157.17 | 207.1 | 3.50 | |

TABLE 7 racemic[9-silafluorenebis(4-(3',5'-di-t-butylphenyl)-2-isopropylindenyl]zirconium dichloride/MAO

| RUN # | Metallocene Catalyst System | Cat Amount (mg) | TEMP. (° C.) | Yield (g) | Efficiency (Kg/g cat) | C2= (delta psi) | H2 (delta psi) | Time split (min.) | $C_2=/C_3=$ flow rates (l/min.) |
|---|---|---|---|---|---|---|---|---|---|
| 72 | 4 | 300 | 60 | 11.8 | 0.04 | — | 0 | 10 | — |
| 73 | 4 | 120 | 70 | 116.8 | 0.97 | — | 10 | 60 | — |
| 74 | 4 | 121 | 70 | 127.6 | 1.1 | — | 10 | 60/90 | 4.0/1.0 |
| 75 | 4 | 62 | 70 | 126.4 | 2.0 | — | 20 | 60 | — |

TABLE 7-continued racemic[9-silafluorenebis(4-(3',5'-di-t-butylphenyl)-2-isopropylindenyl]zirconium dichloride/MAO

| RUN # | Metallocene Catalyst System | Cat Amount (mg) | TEMP. (° C.) | Yield (g) | Efficiency (Kg/g cat) | C2= (delta psi) | H2 (delta psi) | Time split (min.) | C₂=/C₃= flow rates (l/min.) |
|---|---|---|---|---|---|---|---|---|---|
| 76 | 4 | 63 | 70 | 139.5 | 2.2 | — | 35 | 60 | — |
| 77 | 4 | 60 | 70 | 151.4 | 0.40 | — | 20 | 60/90 | 4.2/0.8 |
| 78 | 4 | 62 | 70 | 246.2 | 4.0 | — | 35 | 60/90 | 4.2/0.8 |
| 79 | 4 | 60 | 70 | 218.9 | 3.6 | — | 35 | 60/120 | 4.2/0.8 |
| 80 | 4 | 62 | 70 | 249.8 | 4.0 | — | 50 | 60 | — |
| 81 | 4 | 61 | 70 | 233.1 | 3.8 | — | 35 | 60/120 | 4.4/0.6 |
| 82 | 4 | 61 | 60 | 184.2 | 3.0 | 10 | 20 | 60 | — |
| 83 | 4 | 60 | 60 | 202.6 | 3.4 | 20 | 20 | 60 | — |
| 84 | 4 | 60 | 60 | 209.6 | 3.5 | 30 | 20 | 60 | — |
| 85 | 4 | 60 | 70 | 157.9 | 2.6 | — | 35 | 30/120 | 4.4/0.6 |
| 86 | 4 | 63 | 70 | 200.5 | 3.2 | — | 35 | 60 | — |
| 87 | 4 | 60 | 70 | 223.9 | 3.7 | — | 35 | 60/120 | 4.2/0.8 |
| 88 | 4 | 60 | 70 | 196.1 | 3.3 | — | 35 | 60/180 | 4.2/0.8 |

TABLE 8 racemic[9-silafluorenebis(4-(3',5'-di-t-butylphenyl)-2-isopropylindenyl]zirconium dichloride/MAO

| RUN # | Metallocene Catalyst System | Total Ethylene (wt %) | Ethylene in Rubber (wt %) | Total rubber (wt %) | (Final MFR) (g/10 min.) | Melting Point (° C.) | MW | MWD | IV of Copolymer |
|---|---|---|---|---|---|---|---|---|---|
| 72 | 4 | — | — | — | 0.82 | 160.78 | 381.6 | 2.01 | — |
| 73 | 4 | — | — | — | 2.85 | 159.17 | 267.3 | 1.80 | — |
| 74 | 4 | 4.297 | 32.93 | 13.0 | 3.56 | 161.1 | 255.7 | 2.03 | 2.92 |
| 75 | 4 | — | — | — | 11.53 | 158.83 | 191.5 | 2.25 | — |
| 76 | 4 | — | — | — | 24.03 | 159.43 | 166.6 | 1.98 | — |
| 77 | 4 | 2.449 | 32.63 | 7.5 | 12.0 | 159.7 | 194.7 | 2.11 | 2.06 |
| 78 | 4 | 2.012 | 42.53 | 4.7 | 110.44 | 159.1 | 116.8 | 2.48 | 2.21 |
| 79 | 4 | 3.389 | 40.38 | 8.4 | 32.37 | 158.5 | 173.2 | 2.71 | 2.55 |
| 80 | 4 | — | — | — | 499.99 | 157.9 | 85.7 | 2.25 | — |
| 81 | 4 | 4.093 | 47.35 | 8.6 | 41.24 | 158.57 | 147.0 | 2.32 | 2.87 |
| 82 | 4 | 0.87 | — | — | 9.54 | 151.17 | 204.2 | 2.39 | — |
| 83 | 4 | 1.4 | — | — | 18.53 | 146.17 | 182.3 | 2.14 | — |
| 84 | 4 | 2.4 | — | — | 24.5 | 138.5 | 172.2 | 1.93 | — |
| 85 | 4 | 4.732 | 46.4 | 10.2 | 118.7 | 158.23 | 119.7 | 2.39 | |
| 86 | 4 | — | — | — | 28.17 | 158.37 | | | — |
| 87 | 4 | 3.081 | 44.21 | 7.0 | 61.24 | 158.83 | | | |
| 88 | 4 | — | — | — | 15.7 | 158.77 | | | — |

TABLE 9

[9-silafluorenebis(4-(3',5'-dimethylphenyl)-2-isopropylindene]zirconium dichloride/MAO

| RUN # | Metallocene Catalyst System | TEMP. (° C.) | Cat Amount (mg) | Yield (g) | Efficiency (Kg/g cat) | H2 (delta psi) | Time (min.) |
|---|---|---|---|---|---|---|---|
| 133 | 5 | 60 | 302 | 6.0 | 0.02 | 0 | 60 |
| 134 | 5 | 70 | 121 | 18.4 | 0.15 | 10 | 60 |

TABLE 10

[9-silafluorenebis(4-3',5'-dimethylphenyl)-2-isopropylindene]zirconium dichloride/MAO

| Run # | Metallocene Catalyst System | Final MFR (g/10 min.) | Melting Point (° C.) | MW | MWD |
|---|---|---|---|---|---|
| 133 | 5 | — | 150.9, minor 156.52 | 467.6 | 4.98 |
| 134 | 5 | 32.07 | 156.5 | 104.8 | 2.71 |

TABLE 11

Polymerizations using rac-9-silafluorenebis(2-methylindenyl)zirconium dimethyl

| Run # | T (° C.) | Catalyst Precursor (mg) | Activator (mg) | Yield (g) | Melting Point (° C.) | MW | MWD |
|---|---|---|---|---|---|---|---|
| 135 | 60 | 1.20 | 1.98 | 49.3 | 148.7 | 72610 | 1.93 |
| 136 | 60 | 0.90 | 1.50 | 50.4 | 149.8 | 72215 | 1.97 |

While the present invention has been described and illustrated by reference to particular embodiments, it will be appreciated by those of ordinary skill in the art, that the invention lends itself to many different variations not illustrated herein. For these reasons, then, reference should be made solely to the appended claims for purposes of determining the true scope of the present invention.

We claim:

1. A compound represented by the formula:

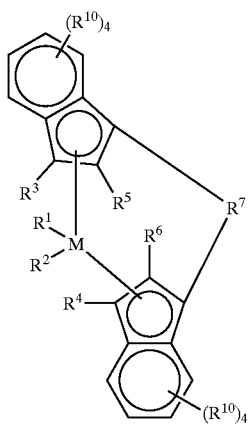

wherein: M is selected from the group consisting of titanium, zirconium, hafnium, vanadium, niobium, tantalum, chromium, molybdenum and tungsten;

$R^1$ and $R^2$ are identical or different, and are one of a hydrogen atom, a $C_1$–$C_{10}$ alkyl group, a $C_1$–$C_{10}$ alkoxy group, a $C_6$–$C_{10}$ aryl group, a $C_6$–$C_{10}$ aryloxy group, a $C_2$–$C_{10}$ alkenyl group, a $C_2$–$C_4$ alkenyl group, a $C_7$–$C_{40}$ arylalkyl group, a $C_7$–$C_{40}$ alkylaryl group, a $C_8$–$C_{40}$ arylalkenyl group, or a halogen atom;

$R^5$ and $R^6$ are identical or different, and are one of a hydrogen atom, a halogen atom, a $C_1$–$C_{10}$ alkyl group which may be halogenated, a $C_6$–$C_{10}$ aryl group which may be halogenated, a $C_2$–$C_{10}$ alkenyl group, a $C_7$–$C_{40}$arylalkyl group, a $C_7$–$C_{40}$ alkylaryl group, a $C_8$–$C_{40}$ arylalkenyl group, a —$NR_2^{15}$, —$SR^{15}$, —$OR^{15}$, —$OSiR_3^{15}$ or —$PR_2^{15}$ radical, wherein $R^{15}$ is one of a halogen atom, a $C_1$–$C_{10}$ alkyl group, or a $C_6$–$C_{10}$ aryl group;

$R^7$ is

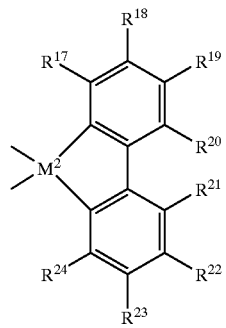

wherein: $R^{17}$ to $R^{24}$ are as defined for $R^1$ and $R^2$, or two or more adjacent radicals $R^{17}$ to $R^{24}$, including $R^{20}$ and $R^{21}$, together with the atoms connecting them form one or more rings;

$M^2$ is carbon, silicon, germanium or tin; and the radicals $R^3$, $R^4$ and $R^{10}$ are identical or different and have the meanings stated for $R^5$ and $R^6$, or two adjacent $R^{10}$ radicals are joined together to form a ring.

2. The compound of claim 1 wherein $M^2$ is silicon.

3. The compound of claim 1 wherein M is zirconium, titanium or hafnium.

4. The compound of claim 1 wherein M is zirconium.

5. The compound of claim 1 wherein $R^5$ and $R^6$ are not hydrogen.

6. The compound of claim 1 wherein $R^{17}$–$R^{24}$ are hydrogen.

* * * * *